(12) United States Patent
Hofmeister et al.

(10) Patent No.: US 10,000,574 B2
(45) Date of Patent: Jun. 19, 2018

(54) COMPOSITIONS COMPRISING POLYPEPTIDES

(75) Inventors: Robert Hofmeister, München (DE); Nadja Prang, Rome (IT); Andreas Wolf, Munich (DE); Frank Hanakam, München (DE); Thomas Urbig, München (DE); Christian Itin, Feldafing (DE); Patrick Baeuerle, Gauting (DE)

(73) Assignee: AMGEN RESEARCH (MUNICH) GMBH, Munich (DE)

( * ) Notice: Subject to any disclaimer, the term of this patent is extended or adjusted under 35 U.S.C. 154(b) by 1957 days.

(21) Appl. No.: 10/580,660

(22) PCT Filed: Nov. 26, 2004

(86) PCT No.: PCT/EP2004/013445
§ 371 (c)(1),
(2), (4) Date: Mar. 8, 2007

(87) PCT Pub. No.: WO2005/052004
PCT Pub. Date: Jun. 9, 2005

(65) Prior Publication Data
US 2007/0249529 A1 Oct. 25, 2007

(30) Foreign Application Priority Data
Nov. 28, 2003 (EP) ..................... 03027511

(51) Int. Cl.
*C07K 16/30* (2006.01)
*C07K 16/28* (2006.01)

(52) U.S. Cl.
CPC .......... *C07K 16/30* (2013.01); *C07K 16/2803* (2013.01); *C07K 16/2809* (2013.01); *C07K 2317/31* (2013.01); *C07K 2317/34* (2013.01); *C07K 2317/56* (2013.01)

(58) Field of Classification Search
None
See application file for complete search history.

(56) References Cited

U.S. PATENT DOCUMENTS

| | | | | |
|---|---|---|---|---|
| 5,917,021 A | * | 6/1999 | Lee | 530/387.3 |
| 7,112,324 B1 | * | 9/2006 | Dorken et al. | 424/133.1 |
| 2002/0142964 A1 | * | 10/2002 | Nissen et al. | 514/12 |
| 2003/0138417 A1 | * | 7/2003 | Kaisheva et al. | 424/130.1 |

FOREIGN PATENT DOCUMENTS

| | | |
|---|---|---|
| EP | 1348715 | 11/2003 |
| WO | WO 99/54440 | 10/1999 |

OTHER PUBLICATIONS

Rudikoff et al. Proc Natl Acad Sci USA 1982 vol. 79 p. 1979.*
MacCallum et al. J. Mol. Biol. (1996) 262, 732-745.*
Pascalis et al. The Journal of Immunology (2002) 169, 3076-3084.*
Casset et al. (2003) BBRC 307, 198-205.*
Vajdos et al. Journal of Molecular Biology. (2002) 320, 415-428.*
Chen et al. J. Mol. Bio. (1999) 293, 865-881.*
Wu et al. J. Mol. Biol. (1999) 294, 151-162.*
Holm et al. Molecular Immunology, (2007) 44, 1075-1084.*
Mueller et al. PNAS vol. 89 pp. 11832-11836, Dec. 1992.*
Kretzchmar et al. (J of Immunological Methods, vol. 195, 1996).*
Arndt et al., "Factors Influencing the Dimer to Monomer Transition of an Antibody Single-Chain Fv Fragment," *Biochemistry*, 37:12918-12926, 1998.
Bruhl, "Depletion of CCR5-expressing cells with bispecific antibodies and chemokine toxins: a new strategy in the treatment of chronic inflammatory diseases and HIV," *J Immunol.*, 166:2420-2426, 2001.
Hoffman et al., "Serial Killing of tumor cells by cytotoxic T cells redirected with a CD19-/CD3-bispecific single-chain antibody construct," *International Journal of Cancer*, 115:98-104, 2005.
Jager et al., "Immune monitoring of tumor cell elimination from malignant ascites during immunotherapy with trifunctional bispecific antibodies," *Eur. J. Cancer*, 37:S60, 2001.
Kretzschmar et al., "High-level exprssion in insect cells and purification of secreted monomeric single-chain Fv antibodies," *J of Immunological Methods*, 195:93-101, 1996.
Kufer et al., "Construction and biological activity of a recombinant bispecific single-chain antibody designed for therapy of minimal residual colorectal cancer," *Cancer Immunol. Immunother.*, 45:193-197, 1997.
Lee et al., "Reversible Dimer Formation and Stability of the Anti-tumour Single-chain Fv Antibody MFE-23 by Neutron Scattering, Analytical Ultracentrifugation, and NMR and FT_IR Spectroscopy," *J. Mol. Biol.*, 320:107-127, 2002.
Loeffler et al., "Efficient elimination of chronic lymphocytic leukaemia B cells by autologous T cells with a bispecific anti-CD19/anti-CD3 single-chain antibody construct," *Leukemia*, 17:900-909, 2003.
Loffler et al., "A recombinant bispecific single-chain antibody, CD19 X CD3, induces rapid and high lymphoma-directed cytotoxicity by unstimulated T lymphocytes," *Blood*, 95:2098-2103, 2000.
Luellau et al., "Development of a downstream process for the isolation and seperation of monoclonal immunoglobulin A monomers, dimers and polymers from cell culture supernatant," *J. Chromatography*, 796:165-175, 1998.

(Continued)

*Primary Examiner* — Laura B Goddard
*Assistant Examiner* — Meera Natarajan
(74) *Attorney, Agent, or Firm* — Marshall, Gerstein & Borun LLP

(57) ABSTRACT

The present invention relates to compositions comprising polypeptides, especially polypeptides capable of specifically binding predetermined antigens. The polypeptide in the composition comprises at least two antigen binding sites. These at least two antigen binding sites are located on a single polypeptide chain. One of the at least two antigen binding sites specifically binds the human CD3 antigen. The polypeptide may exist in both monomeric form and multimeric form. The multimeric form of the polypeptide constitutes no more than 5% of the total weight of the combined monomeric and multimeric forms of said polypeptide.

15 Claims, 6 Drawing Sheets

(56) References Cited

OTHER PUBLICATIONS

Mack et al., "A small bispecific antibody construct expressed as a functional single-chain molecule with high tumor cell cytotoxicity," *PNAS* 92:7021-7025, 1995.

Mack et al., "Biologic properties of a bispecific single-chain antibody directed against 17-1A (EpCAM) and CD3: tumor cell-dependent T cell stimulation and cytotoxic activity," *J Immunol.*, 158:3965-3970, 1997.

Maletz et al., "Bispecific Single-Chain Antibodies as Effective Tools for Eliminating Epithelial Cancer Cells From Human Stem Cell Preparations by Redirected Cell Cytotoxicity," *International Journal of Cancer*, 93:409-416, 2001.

Schoberth et al., "A New Class of Trifunctional Bispecific Antibodies Mediated Efficient Immunological Purging of Peripheral Blood Stem Cells," *Eur. J. Cancer*, 37:S51, 2001.

Worn et al., "Stability Engineering of Antibody Single-Chain Fv Fragments," *J Mol Biology*, 305:989-1010, 2001.

\* cited by examiner

SEQUENCE LISTING

<160> NUMBER OF SEQ ID NOS: 6

<210> SEQ ID NO 1
<211> LENGTH: 504
<212> TYPE: PRT
<213> ORGANISM: artificial sequence
<220> FEATURE:
<223> OTHER INFORMATION: Construct 1: VL(CD19)-VH(CD19)-VH(CD3)-VL(CD3)

<400> SEQUENCE: 1

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
        50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
```

```
                355                 360                 365
Thr Leu Thr Val Ser Ser Val Glu Gly Gly Ser Gly Gly
    370                 375                 380
Ser Gly Ser Gly Gly Val Asp Asp Ile Gln Leu Thr Gln Ser Pro
385                 390                 395                 400
Ala Ile Met Ser Ala Ser Pro Gly Glu Lys Val Thr Met Thr Cys Arg
                405                 410                 415
Ala Ser Ser Val Ser Tyr Met Asn Trp Tyr Gln Gln Lys Ser Gly
                420                 425                 430
Thr Ser Pro Lys Arg Trp Ile Tyr Asp Thr Ser Lys Val Ala Ser Gly
                435                 440                 445
Val Pro Tyr Arg Phe Ser Gly Ser Gly Ser Gly Thr Ser Tyr Ser Leu
                450                 455                 460
Thr Ile Ser Ser Met Glu Ala Glu Asp Ala Ala Thr Tyr Tyr Cys Gln
465                 470                 475                 480
Gln Trp Ser Ser Asn Pro Leu Thr Phe Gly Ala Gly Thr Lys Leu Glu
                485                 490                 495
Leu Lys His His His His His His
                500

<210> SEQ ID NO 2
<211> LENGTH: 505
<212> TYPE: PRT
<213> ORGANISM: artificial sequence
<220> FEATURE:
<223> OTHER INFORMATION: Construct 2: VH(CD19)-VL(CD19)-VH(CD3)-VL(CD3)

<400> SEQUENCE: 2

Gln Val Gln Leu Gln Gln Ser Gly Ala Glu Leu Val Arg Pro Gly Ser
1               5                   10                  15
Ser Val Lys Ile Ser Cys Lys Ala Ser Gly Tyr Ala Phe Ser Ser Tyr
                20                  25                  30
Trp Met Asn Trp Val Lys Gln Arg Pro Gly Gln Gly Leu Glu Trp Ile
            35                  40                  45
Gly Gln Ile Trp Pro Gly Asp Gly Asp Thr Asn Tyr Asn Gly Lys Phe
        50                  55                  60
Lys Gly Lys Ala Thr Leu Thr Ala Asp Glu Ser Ser Ser Thr Ala Tyr
65                  70                  75                  80
Met Gln Leu Ser Ser Leu Ala Ser Glu Asp Ser Ala Val Tyr Phe Cys
                85                  90                  95
Ala Arg Arg Glu Thr Thr Thr Val Gly Arg Tyr Tyr Tyr Ala Met Asp
                100                 105                 110
Tyr Trp Gly Gln Gly Thr Thr Val Thr Val Ser Ser Gly Gly Gly Gly
            115                 120                 125
Ser Gly Gly Gly Gly Ser Gly Gly Gly Gly Ser Asp Ile Gln Leu Thr
        130                 135                 140
Gln Ser Pro Ala Ser Leu Ala Val Ser Leu Gly Gln Arg Ala Thr Ile
145                 150                 155                 160
Ser Cys Lys Ala Ser Gln Ser Val Asp Tyr Asp Gly Asp Ser Tyr Leu
                165                 170                 175
Asn Trp Tyr Gln Gln Ile Pro Gly Gln Pro Pro Lys Leu Leu Ile Tyr
                180                 185                 190
Asp Ala Ser Asn Leu Val Ser Gly Ile Pro Pro Arg Phe Ser Gly Ser
                195                 200                 205
Gly Ser Gly Thr Asp Phe Thr Leu Asn Ile His Pro Val Glu Lys Val
```

-continued

Asp Ala Ala Thr Tyr His Cys Gln Gln Ser Thr Glu Asp Pro Trp Thr
225                 230                 235                 240

Phe Gly Gly Gly Thr Lys Leu Glu Ile Lys Ser Gly Gly Gly Gly Ser
            245                 250                 255

Asp Ile Lys Leu Gln Gln Ser Gly Ala Glu Leu Ala Arg Pro Gly Ala
            260                 265                 270

Ser Val Lys Met Ser Cys Lys Thr Ser Gly Tyr Thr Phe Thr Arg Tyr
            275                 280                 285

Thr Met His Trp Val Lys Gln Arg Pro Gly Gln Gly Leu Glu Trp Ile
            290                 295                 300

Gly Tyr Ile Asn Pro Ser Arg Gly Tyr Thr Asn Tyr Asn Gln Lys Phe
305                 310                 315                 320

Lys Asp Lys Ala Thr Leu Thr Thr Asp Lys Ser Ser Ser Thr Ala Tyr
            325                 330                 335

Met Gln Leu Ser Ser Leu Thr Ser Glu Asp Ser Ala Val Tyr Tyr Cys
            340                 345                 350

Ala Arg Tyr Tyr Asp Asp His Tyr Cys Leu Asp Tyr Trp Gly Gln Gly
            355                 360                 365

Thr Thr Leu Thr Val Ser Ser Val Glu Gly Gly Ser Gly Gly Ser Gly
            370                 375                 380

Gly Ser Gly Gly Ser Gly Val Asp Asp Ile Gln Leu Thr Gln Ser
385                 390                 395                 400

Pro Ala Ile Met Ser Ala Ser Pro Gly Glu Lys Val Thr Met Thr Cys
            405                 410                 415

Arg Ala Ser Ser Ser Val Ser Tyr Met Asn Trp Tyr Gln Gln Lys Ser
            420                 425                 430

Gly Thr Ser Pro Lys Arg Trp Ile Tyr Asp Thr Ser Lys Val Ala Ser
            435                 440                 445

Gly Val Pro Tyr Arg Phe Ser Gly Ser Gly Ser Gly Thr Ser Tyr Ser
            450                 455                 460

Leu Thr Ile Ser Ser Met Glu Ala Glu Asp Ala Ala Thr Tyr Tyr Cys
465                 470                 475                 480

Gln Gln Trp Ser Ser Asn Pro Leu Thr Phe Gly Ala Gly Thr Lys Leu
            485                 490                 495

Glu Leu Lys His His His His His His
            500                 505

<210> SEQ ID NO 3
<211> LENGTH: 504
<212> TYPE: PRT
<213> ORGANISM: artificial sequence
<220> FEATURE:
<223> OTHER INFORMATION: Construct 6: VH(CD3)-VL(CD3)-VH(CD19)-VL(CD19)

<400> SEQUENCE: 3

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr

```
                65                      70                      75                      80
            Met Gln Leu Ser Ser Leu Thr Ser Glu Asp Ser Ala Val Tyr Tyr Cys
                                85                      90                      95

Ala Arg Tyr Tyr Asp Asp His Tyr Cys Leu Asp Tyr Trp Gly Gln Gly
                                100                     105                     110

Thr Thr Leu Thr Val Ser Ser Gly Gly Gly Ser Gly Gly Gly Gly
                                115                     120                     125

Ser Gly Gly Gly Gly Ser Asp Ile Gln Leu Thr Gln Ser Pro Ala Ile
                                130                     135                     140

Met Ser Ala Ser Pro Gly Glu Lys Val Thr Met Thr Cys Arg Ala Ser
            145                     150                     155                     160

Ser Ser Val Ser Tyr Met Asn Trp Tyr Gln Gln Lys Ser Gly Thr Ser
                                165                     170                     175

Pro Lys Arg Trp Ile Tyr Asp Thr Ser Lys Val Ala Ser Gly Val Pro
                                180                     185                     190

Tyr Arg Phe Ser Gly Ser Gly Ser Gly Thr Ser Tyr Ser Leu Thr Ile
                                195                     200                     205

Ser Ser Met Glu Ala Glu Asp Ala Ala Thr Tyr Tyr Cys Gln Gln Trp
                                210                     215                     220

Ser Ser Asn Pro Leu Thr Phe Gly Ala Gly Thr Lys Leu Glu Leu Lys
            225                     230                     235                     240

Ser Gly Gly Gly Gly Ser Gln Val Gln Leu Gln Gln Ser Gly Ala Glu
                                245                     250                     255

Leu Val Arg Pro Gly Ser Ser Val Lys Ile Ser Cys Lys Ala Ser Gly
                                260                     265                     270

Tyr Ala Phe Ser Ser Tyr Trp Met Asn Trp Val Lys Gln Arg Pro Gly
                                275                     280                     285

Gln Gly Leu Glu Trp Ile Gly Gln Ile Trp Pro Gly Asp Gly Asp Thr
                                290                     295                     300

Asn Tyr Asn Gly Lys Phe Lys Gly Lys Ala Thr Leu Thr Ala Asp Glu
            305                     310                     315                     320

Ser Ser Ser Thr Ala Tyr Met Gln Leu Ser Ser Leu Ala Ser Glu Asp
                                325                     330                     335

Ser Ala Val Tyr Phe Cys Ala Arg Arg Glu Thr Thr Val Gly Arg
                                340                     345                     350

Tyr Tyr Tyr Ala Met Asp Tyr Trp Gly Gln Gly Thr Thr Val Thr Val
                                355                     360                     365

Ser Ser Gly Gly Gly Gly Ser Gly Gly Gly Gly Ser Gly Gly Gly Gly
                                370                     375                     380

Ser Asp Ile Gln Leu Thr Gln Ser Pro Ala Ser Leu Ala Val Ser Leu
            385                     390                     395                     400

Gly Gln Arg Ala Thr Ile Ser Cys Lys Ala Ser Gln Ser Val Asp Tyr
                                405                     410                     415

Asp Gly Asp Ser Tyr Leu Asn Trp Tyr Gln Gln Ile Pro Gly Gln Pro
                                420                     425                     430

Pro Lys Leu Leu Ile Tyr Asp Ala Ser Asn Leu Val Ser Gly Ile Pro
                                435                     440                     445

Pro Arg Phe Ser Gly Ser Gly Ser Gly Thr Asp Phe Thr Leu Asn Ile
                                450                     455                     460

His Pro Val Glu Lys Val Asp Ala Ala Thr Tyr His Cys Gln Gln Ser
            465                     470                     475                     480

Thr Glu Asp Pro Trp Thr Phe Gly Gly Gly Thr Lys Leu Glu Ile Lys
                                485                     490                     495
```

```
Ser Gly His His His His His His
        500

<210> SEQ ID NO 4
<211> LENGTH: 503
<212> TYPE: PRT
<213> ORGANISM: artificial sequence
<220> FEATURE:
<223> OTHER INFORMATION: Construct 8: VH(CD3)-VL(CD3)-VL(CD19)-VH(CD19)

<400> SEQUENCE: 4

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Ser Gly Gly Gly Gly
        115                 120                 125

Ser Gly Gly Gly Gly Ser Asp Ile Gln Leu Thr Gln Ser Pro Ala Ile
    130                 135                 140

Met Ser Ala Ser Pro Gly Glu Lys Val Thr Met Thr Cys Arg Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Val Ala Ser Gly Val Pro
            180                 185                 190

Tyr Arg Phe Ser Gly Ser Gly Ser Gly Thr Ser Tyr Ser Leu Thr Ile
        195                 200                 205

Ser Ser Met Glu Ala Glu Asp Ala Ala Thr Tyr Tyr Cys Gln Gln Trp
    210                 215                 220

Ser Ser Asn Pro Leu Thr Phe Gly Ala Gly Thr Lys Leu Glu Leu Lys
225                 230                 235                 240

Ser Gly Gly Gly Gly Ser Asp Ile Gln Leu Thr Gln Ser Pro Ala Ser
                245                 250                 255

Leu Ala Val Ser Leu Gly Gln Arg Ala Thr Ile Ser Cys Lys Ala Ser
            260                 265                 270

Gln Ser Val Asp Tyr Asp Gly Asp Ser Tyr Leu Asn Trp Tyr Gln Gln
        275                 280                 285

Ile Pro Gly Gln Pro Pro Lys Leu Leu Ile Tyr Asp Ala Ser Asn Leu
    290                 295                 300

Val Ser Gly Ile Pro Pro Arg Phe Ser Gly Ser Gly Ser Gly Thr Asp
305                 310                 315                 320

Phe Thr Leu Asn Ile His Pro Val Glu Lys Val Asp Ala Ala Thr Tyr
                325                 330                 335

His Cys Gln Gln Ser Thr Glu Asp Pro Trp Thr Phe Gly Gly Gly Thr
            340                 345                 350
```

-continued

```
Lys Leu Glu Ile Lys Gly Gly Gly Ser Gly Gly Gly Ser Gly
            355                 360                 365

Gly Gly Gly Ser Gln Val Gln Leu Gln Gln Ser Gly Ala Glu Leu Val
        370                 375                 380

Arg Pro Gly Ser Ser Val Lys Ile Ser Cys Lys Ala Ser Gly Tyr Ala
385                 390                 395                 400

Phe Ser Ser Tyr Trp Met Asn Trp Val Lys Gln Arg Pro Gly Gln Gly
                405                 410                 415

Leu Glu Trp Ile Gly Gln Ile Trp Pro Gly Asp Gly Asp Thr Asn Tyr
            420                 425                 430

Asn Gly Lys Phe Lys Gly Lys Ala Thr Leu Thr Ala Asp Glu Ser Ser
        435                 440                 445

Ser Thr Ala Tyr Met Gln Leu Ser Ser Leu Ala Ser Glu Asp Ser Ala
    450                 455                 460

Val Tyr Phe Cys Ala Arg Arg Glu Thr Thr Thr Val Gly Arg Tyr Tyr
465                 470                 475                 480

Tyr Ala Met Asp Tyr Trp Gly Gln Gly Thr Thr Val Thr Val Ser Ser
                485                 490                 495

Gly His His His His His
            500

<210> SEQ ID NO 5
<211> LENGTH: 504
<212> TYPE: PRT
<213> ORGANISM: artificial sequence
<220> FEATURE:
<223> OTHER INFORMATION: Construct 5: VL(CD3)-VH(CD3)-VH(CD19)-VL(CD19)

<400> SEQUENCE: 5

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Gly Gly Gly Ser Gly
            100                 105                 110

Gly Gly Gly Ser Gly Gly Gly Ser Asp Ile Lys Leu Gln Gln Ser
        115                 120                 125

Gly Ala Glu Leu Ala Arg Pro Gly Ala Ser Val Lys Met Ser Cys Lys
    130                 135                 140

Thr Ser Gly Tyr Thr Phe Thr Arg Tyr Thr Met His Trp Val Lys Gln
145                 150                 155                 160

Arg Pro Gly Gln Gly Leu Glu Trp Ile Gly Tyr Ile Asn Pro Ser Arg
                165                 170                 175

Gly Tyr Thr Asn Tyr Asn Gln Lys Phe Lys Asp Lys Ala Thr Leu Thr
            180                 185                 190

Thr Asp Lys Ser Ser Ser Thr Ala Tyr Met Gln Leu Ser Ser Leu Thr
        195                 200                 205
```

Ser Glu Asp Ser Ala Val Tyr Tyr Cys Ala Arg Tyr Asp Asp His
210                 215                 220

Tyr Cys Leu Asp Tyr Trp Gly Gln Gly Thr Thr Leu Thr Val Ser Ser
225                 230                 235                 240

Ser Gly Gly Gly Gly Ser Gln Val Gln Leu Gln Gln Ser Gly Ala Glu
            245                 250                 255

Leu Val Arg Pro Gly Ser Ser Val Lys Ile Ser Cys Lys Ala Ser Gly
            260                 265                 270

Tyr Ala Phe Ser Ser Tyr Trp Met Asn Trp Val Lys Gln Arg Pro Gly
            275                 280                 285

Gln Gly Leu Glu Trp Ile Gly Gln Ile Trp Pro Gly Asp Gly Asp Thr
290                 295                 300

Asn Tyr Asn Gly Lys Phe Lys Gly Lys Ala Thr Leu Thr Ala Asp Glu
305                 310                 315                 320

Ser Ser Ser Thr Ala Tyr Met Gln Leu Ser Ser Leu Ala Ser Glu Asp
            325                 330                 335

Ser Ala Val Tyr Phe Cys Ala Arg Arg Glu Thr Thr Thr Val Gly Arg
            340                 345                 350

Tyr Tyr Tyr Ala Met Asp Tyr Trp Gly Gln Gly Thr Thr Val Thr Val
            355                 360                 365

Ser Ser Gly Gly Gly Gly Ser Gly Gly Gly Ser Gly Gly Gly Gly
            370                 375                 380

Ser Asp Ile Gln Leu Thr Gln Ser Pro Ala Ser Leu Ala Val Ser Leu
385                 390                 395                 400

Gly Gln Arg Ala Thr Ile Ser Cys Lys Ala Ser Gln Ser Val Asp Tyr
            405                 410                 415

Asp Gly Asp Ser Tyr Leu Asn Trp Tyr Gln Gln Ile Pro Gly Gln Pro
            420                 425                 430

Pro Lys Leu Leu Ile Tyr Asp Ala Ser Asn Leu Val Ser Gly Ile Pro
            435                 440                 445

Pro Arg Phe Ser Gly Ser Gly Ser Gly Thr Asp Phe Thr Leu Asn Ile
            450                 455                 460

His Pro Val Glu Lys Val Asp Ala Ala Thr Tyr His Cys Gln Gln Ser
465                 470                 475                 480

Thr Glu Asp Pro Trp Thr Phe Gly Gly Gly Thr Lys Leu Glu Ile Lys
            485                 490                 495

Ser Gly His His His His His His
            500

<210> SEQ ID NO 6
<211> LENGTH: 503
<212> TYPE: PRT
<213> ORGANISM: artificial sequence
<220> FEATURE:
<223> OTHER INFORMATION: Construct 7: VL(CD3)-VH(CD3)-VL(CD19)-VH(CD19)

<400> SEQUENCE: 6

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
            35                  40                  45

Asp Thr Ser Lys Val Ala Ser Gly Val Pro Tyr Arg Phe Ser Gly Ser
50                  55                  60

```
Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser Asn Pro Leu Thr
                 85                  90                  95

Phe Gly Ala Gly Thr Lys Leu Glu Leu Lys Gly Gly Gly Gly Ser Gly
            100                 105                 110

Gly Gly Gly Ser Gly Gly Gly Gly Ser Asp Ile Lys Leu Gln Gln Ser
            115                 120                 125

Gly Ala Glu Leu Ala Arg Pro Gly Ala Ser Val Lys Met Ser Cys Lys
            130                 135                 140

Thr Ser Gly Tyr Thr Phe Thr Arg Tyr Thr Met His Trp Val Lys Gln
145                 150                 155                 160

Arg Pro Gly Gln Gly Leu Glu Trp Ile Gly Tyr Ile Asn Pro Ser Arg
                165                 170                 175

Gly Tyr Thr Asn Tyr Asn Gln Lys Phe Lys Asp Lys Ala Thr Leu Thr
            180                 185                 190

Thr Asp Lys Ser Ser Ser Thr Ala Tyr Met Gln Leu Ser Ser Leu Thr
            195                 200                 205

Ser Glu Asp Ser Ala Val Tyr Tyr Cys Ala Arg Tyr Tyr Asp Asp His
210                 215                 220

Tyr Cys Leu Asp Tyr Trp Gly Gln Gly Thr Thr Leu Thr Val Ser Ser
225                 230                 235                 240

Ser Gly Gly Gly Gly Ser Asp Ile Gln Leu Thr Gln Ser Pro Ala Ser
            245                 250                 255

Leu Ala Val Ser Leu Gly Gln Arg Ala Thr Ile Ser Cys Lys Ala Ser
            260                 265                 270

Gln Ser Val Asp Tyr Asp Gly Asp Ser Tyr Leu Asn Trp Tyr Gln Gln
            275                 280                 285

Ile Pro Gly Gln Pro Pro Lys Leu Leu Ile Tyr Asp Ala Ser Asn Leu
            290                 295                 300

Val Ser Gly Ile Pro Pro Arg Phe Ser Gly Ser Gly Ser Gly Thr Asp
305                 310                 315                 320

Phe Thr Leu Asn Ile His Pro Val Glu Lys Val Asp Ala Ala Thr Tyr
                325                 330                 335

His Cys Gln Gln Ser Thr Glu Asp Pro Trp Thr Phe Gly Gly Gly Thr
            340                 345                 350

Lys Leu Glu Ile Lys Gly Gly Gly Ser Gly Gly Gly Gly Ser Gly
            355                 360                 365

Gly Gly Gly Ser Gln Val Gln Leu Gln Gln Ser Gly Ala Glu Leu Val
            370                 375                 380

Arg Pro Gly Ser Ser Val Lys Ile Ser Cys Lys Ala Ser Gly Tyr Ala
385                 390                 395                 400

Phe Ser Ser Tyr Trp Met Asn Trp Val Lys Gln Arg Pro Gly Gln Gly
                405                 410                 415

Leu Glu Trp Ile Gly Gln Ile Trp Pro Gly Asp Gly Asp Thr Asn Tyr
            420                 425                 430

Asn Gly Lys Phe Lys Gly Lys Ala Thr Leu Thr Ala Asp Glu Ser Ser
            435                 440                 445

Ser Thr Ala Tyr Met Gln Leu Ser Ser Leu Ala Ser Glu Asp Ser Ala
450                 455                 460

Val Tyr Phe Cys Ala Arg Arg Glu Thr Thr Thr Val Gly Arg Tyr Tyr
465                 470                 475                 480
```

```
Tyr Ala Met Asp Tyr Trp Gly Gln Gly Thr Thr Val Thr Val Ser Ser
            485                 490                 495
Gly His His His His His His
            500
```

COMPOSITIONS COMPRISING POLYPEPTIDES

This application is a national phase application under 35 U.S.C. § 371 of International Application No. PCT/EP2004/013445 filed 26 Nov. 2004, which claims priority to European Application No. 03027511.9 filed 28 Nov. 2003. The entire text of each of the above-referenced disclosures is specifically incorporated herein by reference without disclaimer.

The present invention relates to compositions comprising polypeptides, especially polypeptides capable of specifically binding to predetermined antigens via epitopes on said antigens. A preferred composition is a pharmaceutical composition. The present invention also relates to a method of producing an enriched composition in which the amount of a polypeptide in monomeric form has been enriched relative to other multimeric forms of the polypeptide. The present invention also relates to an enriched composition produced by the above method. The present invention further relates to methods for the prevention, treatment or amelioration of various diseases. Finally, the present invention relates to the use of compositions for producing a medicament for the prevention, treatment or amelioration of these various diseases.

With the advent of standardized methods of producing recombinant polypeptides and proteins, such recombinant species are increasingly being employed as the active therapeutic agents in pharmaceutical compositions for the treatment of human disease states. Given the number of companies, research organizations and university laboratories engaging in the development of recombinant therapeutic polypeptides and proteins, the number of medicinal compositions in which the therapeutic effect is attributable to a recombinantly produced polypeptide or protein can only be expected to increase in the future.

Due to their high binding selectivity and affinity, the immunoglobulins ("Igs"), or antibodies, represent one especially relevant class of proteins of high therapeutic potential. Of particular interest in recent years have been recombinantly produced single chain antibodies in both monospecific and bispecific forms. Monospecific single chain antibodies are disclosed for example in U.S. Pat. No. 4,946,778. A bispecific single chain antibody is disclosed for example in U.S. Pat. No. 5,091,513. Such bispecific single chain antibodies can be of particular therapeutic relevance, since the two distinct functionalities within such a species can efficiently and selectively bring two distinct epitopes, that is in most cases two distinct antigens in vivo together spatially. Due to the fact that a bispecific single chain molecule unites two antigen binding sites on a single contiguous polypeptide chain, such molecules overcome the problems of recombinant producability experienced for full Igs due for example to the latter's comprising an Fc portion.

Of particular therapeutic interest has been the development of recombinantly produced antibodies, for example bispecific single chain antibodies, which are capable of specifically binding to the human CD3 antigen.

The human CD3 antigen is present on both helper T cells and cytotoxic T cells. The latter, namely cytotoxic T cells, are responsible for the killing of invading or infected cells against which the cytotoxic T cells have been activated. Human CD3 denotes an antigen which is expressed on T cells as part of the multimolecular T cell complex and which comprises three different chains: CD3-epsilon, CD3-delta and CD3-gamma.

The activation of the cytotoxic potential of T cells is a complex phenomenon which requires the interplay of multiple proteins. The T cell receptor ("TCR") protein is a membrane bound disulfide-linked heterodimer consisting of two different glycoprotein subunits. The TCR recognizes and binds foreign peptidic antigen which itself has been bound by a member of the highly diverse class of major histocompatibility ("MHC") proteins and has been presented, bound to the MHC, on the surface of antigen presenting cells ("APCs").

Although the variable TCR binds foreign antigen as outlined above, signalling to the T cell that this binding has taken place depends on the presence of other, invariant, signalling proteins associated with the TCR. These signalling proteins in associated form are collectively referred to as the CD3 complex.

In summary, the activation of T cell cytotoxicity normally depends first on the binding of the TCR with an MHC protein, itself bound to foreign antigen, located on a separate cell. Only when this initial TCR-MHC binding has taken place can the CD3-dependent signalling cascade responsible for T cell clonal expansion and, ultimately, T cell cytotoxicity ensue.

However, it has previously been found that certain recombinantly produced, polypeptidic antigen binding sites which specifically bind to at least part of the human CD3 antigen have the ability to activate T cells to exert a cytotoxic effect on other cells in the absence of independent TCR-MHC binding. This means that T cells may become cytotoxically active in a clonally independent fashion, i.e. in a manner which is independent of the specific TCR clone carried by the T cell. This allows an activation of the entire T cell compartment rather than only specific T cells of a certain clonal identity. Such molecules have been disclosed in WO 99/54440; Mack, J. Immunol. (1997) 158, 3965-70; Mack, PNAS (1995) 92, 7021-5; Kufer, Cancer Immunol. Immunother. (1997) 45, 193-7; Löffler, Blood (2000) 95, 2098-103; Brohl, J. Immunol. (2001) 166, 2420-6.

The type of biological activity described above, i.e. the ability of a polypeptide to selectively (re)direct the cytotoxic potential of cytotoxic T cells against predetermined target cells such that the latter become lysed, can be of great therapeutic relevance. Specifically, compositions of such polypeptides as those described in the previous paragraph can be and have been effectively used as part of a regimen of therapy entailing the destruction of target cells associated with particular diseases. In particular, such diseases include cancerous states in which transformed cells are the target cells destined for destruction.

In addition to having the sort of biological activity described above, i.e. the ability to direct the cytotoxicity of T cells to target cells intended for destruction, compositions comprising polypeptides of the sort described above will often manifest other additional types of biological activities unrelated to the lysis of target cells. Such additional biological activities may or may not be beneficial and, if such a composition is intended for administration to a patient, stand to complicate the constructing of a therapeutic regimen. It would therefore be desirable to eliminate such additional types of biological activities to the greatest extent possible in such a composition, so that the type of biological activity manifested by the resulting composition remains as homogeneous as possible.

It is therefore an object of the invention to provide a composition which overcomes the above difficulties.

Accordingly, the present invention provides a composition with a polypeptide. The polypeptide comprises at least two antigen binding sites, wherein said at least two antigen binding sites are located on a single polypeptide chain, and wherein one of said at least two antigen binding sites specifically binds the human CD3 antigen;

said polypeptide may exist in both monomeric form and multimeric form, said monomeric form being said single polypeptide chain (with the at least two antigen binding sites) and said multimeric form comprising at least two of said single polypeptide chains non-covalently associated with one another, thereby comprising at least four antigen binding sites; and said multimeric form of said polypeptide constitutes no more than 5% of the total weight of the combined monomeric and multimeric forms of said polypeptide.

The terms "multimeric polypeptide", "polypeptide in multimeric form", "multimer", etc as used herein are equivalent terms and are contemplated as meaning (i) different isoforms within a population of polypeptide molecules multimeric to the same degree (e.g. different dimeric isoforms), and/or (ii) a population of polypeptide molecules which are multimeric to different degrees (e.g. dimers, trimers, etc.).

The term "antigen binding site" is to be understood as a portion of secondary and/or tertiary polypeptide structure which specifically binds an antigen of interest in a non-covalent manner via an epitope of the antigen. Hereinafter, it should be borne in mind that antigens are bound via a specific epitope or via specific epitopes of such antigens. "Specific" binding denotes the ability to discriminate between different antigens as potential binding partners to such an extent that, from a pool of a plurality of different antigens as potential binding partners, only the antigen of interest is bound, or is significantly bound. Within the meaning of the invention, an antigen is "significantly" bound when, from among a pool of equally accessible different antigens as potential binding partners, the antigen of interest is bound at least 10-fold, preferably 50-fold, most preferably 100-fold or greater more frequently (in a kinetic sense) than other antigens which are not the antigen of interest.

Whereas one of the at least two antigen binding sites of the polypeptide comprised in the composition of the invention specifically binds the human CD3 antigen, the at least one other antigen binding site of this polypeptide is allowed to specifically bind any other antigen(or epitope) of interest ("target antigen"). Preferably, the target antigen is an antigen expressed on the surface of a cell, wherein the cell expressing the target antigen/epitope may be a free cell, such as a lymphocyte in the bloodstream, or may form part of a solid tissue. In this manner, the polypeptide comprised in the composition of the invention may with one arm (i.e. one antigen binding site, or the "target antigen binding site") specifically bind to the target antigen, while a/the second arm (i.e. another/the other antigen binding site, or the "effector antigen binding site") of the polypeptide comprised in the composition specifically binds to and activates, via the human CD3 antigen, a cytotoxic T cell in a clonally independent fashion as described above. In this manner, the polypeptide comprised in the composition according to the invention may be generally employed as part of a therapeutic regimen to specifically destroy, via the cytotoxic T cell, a certain cell type.

As implied above, the polypeptide comprised in the composition according to the invention is thus biologically active. The terms "biologically active" and "biological activity" as used herein denote the nature of an effect caused by the polypeptide comprised in the composition according to the invention when said polypeptide is placed in an in vitro, ex vivo or in vivo setting. As used herein, biological activity therefore refers to types of biological effects elicited rather than a certain effect's magnitude.

It has been surprisingly found that the biological activity of the monomeric form of the polypeptide comprised in the inventive composition is much more homogeneous than that of the multimeric form of this polypeptide. That is to say the monomeric form of the polypeptide demonstrates a single type of biological activity (i.e. activation and redirection of the cytotoxic activity of T cells against target cells intended for destruction), whereas the multimeric form, for example the dimeric form of the polypeptide demonstrates multiple types of biological activity which are different than that manifested by the monomeric form of the polypeptide.

Without being bound by theory, it is believed that the greater diversity of biological activity observed for the multimeric form of the polypeptide comprised in the inventive composition might be due at least in part to the greater number of modes for molecular association available for the multimer as compared to the monomer. That is to say that statistically, there exist a greater number of ways a multimeric species composed of a plurality of single polypeptide chains may associate and become folded than exist for the corresponding monomeric species composed of only one single polypeptide chain. This idea is borne out by a number of findings of the inventors and are discussed in detail hereinafter.

The monomeric species of the polypeptide comprised in the inventive composition exhibits a single biological activity. As explained above, this is the ability to recruit the cytotoxic T cells ("CTLs") against other cells which are not CTLs, and which bear on their surface an antigen which is specifically bound by the/a target antigen binding site.

While also partially manifesting a biological activity as observed for the monomeric species, one or more of the multimeric species of said polypeptide also give rise to additional biological activities. It was for example observed that the multimeric polypeptide species led to a decrease in the number of CTLs present in a sample. While not being bound by theory, the inventors believe that this biological activity is likely due to intermolecular association of at least two molecules of monomer polypeptide via their respective antigen binding sites. In this way, a multimeric species is formed in which, for example, the target antigen binding sites mutually engage one another, and thus become unavailable for binding target antigen, whereas each effector antigen binding site specific for the human CD3 antigen remains free to bind a respective CD3 antigen. In this way, a species is formed which is capable of specifically binding at least two distinct molecules of the human CD3 antigen by identical epitopes. Such a species would be capable of simultaneously binding at least two separate CTLs, a scenario in which one of these at least two CTLs might exert its cytotoxic effect on any other of the at least two CTLs. This type of biological activity, in which other cells than the target cells intended for destruction (i.e. the cytotoxic T cells themselves) are lysed, stands to decrease the overall number of CTLs present in a sample. This stands to decrease the number of such cytotoxic T cells available for participating in the type of biological activity manifested by the monomeric species, namely the selective destruction, via T cell mediated lysis, of diseased target cells.

In addition, the inventors have recognized that the multimeric forms of the polypeptide as comprised in the inventive composition are able to activate CTLs even in the absence of other types of non-CTL cells. Normally, the monomeric species of the polypeptide comprised in the inventive composition activates the cytotoxic potential of CTLs only in the presence of the cells ("target cells") displaying the antigen which is bound by the target antigen binding site, which cells are accordingly intended for destruction by the CTLs. Activation of CTLs by the polypeptide of the instant composition only in the presence of such target cells advantageously prevents a possible misdirection of cytotoxic activity of CTLs to non-target cells not intended for destruction.

The inventors have also found that the tendency to form a multimeric species, especially a dimeric species, is a property of this class of polypeptides in general, namely single polypeptide chains comprising both a binding site for the human CD3 antigen and a binding site for another target antigen other than the human CD3 antigen. The additional biological activities above may therefore be expected for any polypeptide of this sort, regardless of the specificity of the target antigen binding site.

As follows from the above explanations, a composition comprising only a minimal, controlled amount of polypeptide in multimeric form and wherein total polypeptide is substantially in the monomeric form will demonstrate a more homogeneous biological activity than a composition containing a greater amount of multimeric polypeptide. By prescribing an upper limit for the amount of multimeric polypeptide in the composition of the invention, a composition is obtained for which the degree of homogeneity in biological activity is controlled and predictable. Controllability and predictability of biological activity are two features which are preferable for compositions contemplated for administration as part of a therapeutic regimen.

According to one embodiment of the composition according to the invention, the multimeric form of the polypeptide constitutes no more than 4%, preferably no more than 3%, more preferably no more than 2%, even more preferably no more than 1%, yet more preferably no more than 0.5% of the total combined weight of polypeptide in both monomeric and multimeric forms in the composition. Most preferably, the multimeric forms of the polypeptide constitute only or even less than the detectable limit of the multimeric forms of the polypeptide in the composition, the vast majority of polypeptide being present in the composition in a monomeric form.

The terms "detectable limit" and "detection limit" as used herein are equivalent terms and are to be understood as denoting an amount of multimeric polypeptide in the instant composition below which no detection of said multimeric polypeptide at all is possible, even when applying the most stringent assay with its most stringent conditions. Suitable methods for determining the amount of multimeric polypeptide in the instant composition include any method of detecting polypeptide species, for example by non-denaturing polyacrylamide gel electrophoresis wherein proteins are stained in the gel with Coomassie brilliant blue or silver nitrate, by Western blot analysis or chromatographic methods such as size exclusion HPLC. Preferably, monitoring the amount of multimeric polypeptide present in the composition can best be accomplished by analytical size exclusion HPLC. By the nature of the term, the "detectable limit" will depend on the sensitivity of the particular detection method used to assay the amount of multimeric form of polypeptide present in a given composition. In addition, the "detectable" limit will understandably depend on how stringently the assay parameters are applied for a given method of choice.

In a further embodiment, the multimeric form of the polypeptide as described above is exclusively the dimeric form of the polypeptide. The "dimeric form" is to be understood as a species comprising two single polypeptide chains, wherein the two single polypeptide chains are non-covalently associated with one another.

Contemplated is a composition comprising a polypeptide which itself comprises two antigen binding sites, and wherein each antigen binding site comprises a variable region from a heavy chain of an antibody (VH) and a variable region from a light chain of an antibody (VL), each VH/VL pair having specificity for a different epitope, preferably for a different antigen, one of which is the human CD3 antigen. The VH and VL regions within a given antigen binding site may be derived from the same or different antibodies. The anti-CD3 binding site may be located at either the N- or C-terminus of the polypeptide. Within the meaning of the instant invention, "VH/VL" or "VH/VL pair" is to be understood as denoting any order of connectivity; either VH-VL or VL-VH. While direct covalent (peptide) attachment of the C-terminal amino acid of a VH or VL region to the N-terminal amino acid of a VL or VH region, respectively, is theoretically possible, one of ordinary skill in the art will understand that such a direct peptide linkage often confers too few spatial degrees of freedom to allow the VH and VL region to associate such that their respective CDR regions can form a single unified antigen binding site. One of skill in the art will therefore understand that such non-covalent association of VH and VL regions consistent with the maintenance of the ability to specifically bind an antigen of choice will often make the inclusion of a peptide linker interposed between the VH and VL regions preferable. Such a peptide linker may take the form of linkers disclosed in the art, for example in EP 0 623 679 B1, U.S. Pat. No. 5,258,498, EP 0 573 551 B1 and U.S. Pat. No. 5,525,491.

One of skill in the art will appreciate that such a molecule might be expected to form a number of different dimeric forms. It might for instance be expected that the VH and VL regions making up the target antigen binding site of one monomeric polypeptide molecule would associate in a linear, anti-parallel fashion with the respective VL and VH regions making up the target antigen binding site of another monomeric polypeptide molecule. This would yield a dimeric polypeptide in which the two antigen binding sites specific for the human CD3 antigen would remain free to specifically bind to two separate human CD3 antigens. It might also be expected that the VH and VL regions making up the CD3 antigen binding specificity of one monomeric polypeptide molecule would associate in a linear antiparallel fashion with the respective VL and VH regions making up the CD3 antigen binding specificity of another monomeric polypeptide molecule. This would yield a dimeric polypeptide in which the two antigen binding sites specific for the target antigen would remain free to specifically bind to two separate target antigens. Also contemplated are pairings between either VH and/or VL regions from the target antigen binding site in one monomeric polypeptide molecule with either VH and/or VL regions from the effector antigen binding site specific for the human CD3 antigen in another monomeric polypeptide molecule. Here, one might expect that the resulting dimeric polypeptide molecule would retain the ability to at least partially bind to each of the human CD3 antigen and the target antigen in a specific manner. The above examples are not limiting in terms of the different species of dimeric polypeptide which may be formed by the polypeptide comprised in the composition of the invention. Clearly, a plurality of different dimeric species can be contemplated, possibly explaining the variegated biological activity observed for multimeric, in particular for dimeric polypeptide.

According to another embodiment of the invention, the composition may comprise polypeptides in which a single antigen binding site comprises two non-covalently associated VH regions on the same polypeptide chain, the two VH regions being separated by a peptide linker as described above, or two non-covalently associated VL regions on the same polypeptide chain, the two VL regions being separated by a peptide linker as described above.

It is envisioned that the VH and/or VL regions of a given antigen binding site may be derived from different sources, for example from two different monoclonal antibodies which may or may not originate from two organisms of the same species, or may be modified (i.e. chimeric, truncated, humanized, deimmunized, etc.).

In an especially preferred embodiment, the polypeptide comprised in the instant composition comprises two antigen binding sites, wherein each antigen binding site comprises one VH and one VL region. In this embodiment, the two antigen binding sites are covalently connected to one another through a short peptide spacer, and each antigen binding site specifically binds a different antigen. As such, a polypeptide according to this embodiment would be represented by the generic formula

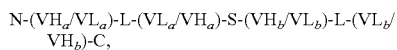

$$N\text{-}(VH_a/VL_a)\text{-}L\text{-}(VL_a/VH_a)\text{-}S\text{-}(VH_b/VL_b)\text{-}L\text{-}(VL_b/VH_b)\text{-}C,$$

where:
a respective pair "VH/VL" or "VL/VH" represents a mutually exclusive option for choosing either VH or VL at that position;
"a" and "b" (in subscript) represent specificity for antigen a and b, respectively;
"L" represents a peptide linker covalently connecting a respective VH and VL or VL and VH within a given single antigen binding site, as discussed above;
"S" represents a peptide spacer, which is a polypeptide region covalently connecting the antigen binding site specifically binding antigen a with the antigen binding site specifically binding antigen b; and
"N" and "C" represent the respective N- and C-termini of the polypeptide.

As such, the present embodiment envisions a composition as set out herein comprising a polypeptide with two distinct antigen binding sites, wherein each antigen binding site comprises a VH region and a VL region connected by a peptide linker, and wherein the two antigen binding sites are connected through a single polypeptide spacer. Thus a single polypeptide chain is created on which two antigen binding sites of different specificities are located. One of skill in the art will recognize a species of this general form as a "bispecific single chain antibody".

It is within the scope of the composition of the invention that the polypeptide comprised therein and as represented by the generic formula above may optionally include other functionalities such as a His-tag or a Flag-tag or other forms of functional labels.

In one particularly preferred embodiment of the invention the composition comprises a polypeptide in which the other of the at least two antigen binding sites, i.e. the target antigen binding site, specifically binds the human CD19 antigen. The human CD19 antigen is expressed in the whole human B lineage from the pro B cell to the mature B cell, it is not shed, is uniformly expressed on all lymphoma cells, and is absent from stem cells. Thus, a composition according to this embodiment, namely one comprising a polypeptide with an antigen binding site which specifically binds the human CD3 antigen as well as an antigen binding site which specifically binds the human CD19 antigen, is of great potential value as a therapeutic. The biological activity of the monomeric form of the polypeptide comprised in a composition advantageously recruits the cytotoxic potential of T cells against B cells in a subject (as explained above). By controlling the multimer:monomer ratio of polypeptide as set out above, a composition is obtained which can advantageously be used to treat B cell-related disorders in an extremely controlled and therefore therapeutically efficacious manner.

Especially preferred is a composition in which the polypeptide with binding specificities for both the human CD3 antigen and the human CD19 antigen has an amino acid sequence equivalent to, or substantially equivalent to any one of those set out in SEQ ID NOs: 1-6 as follows:
Schematic representation of SEQ ID NO 1: VL(CD19)-L-VH(CD19)-S-VH(CD3)-L-VL(CD3);
Schematic representation of SEQ ID NO 2: VH(CD19)-L-VL(CD19)-S-VH(CD3)-L-VL(CD3);
Schematic representation of SEQ ID NO 3: VH(CD3)-L-VL(CD3)-S-VH(CD19)-L-VL(CD19); or
Schematic representation of SEQ ID NO 4: VH(CD3)-L-VL(CD3)-S-VL(CD19)-L-VH(CD19),
Schematic representation of SEQ ID NO 5: VL(CD3)-L-VH(CD3)-S-VH(CD19)-L-VL(CD19),
Schematic representation of SEQ ID NO 6: VL(CD3)-L-VH(CD3)-S-VL(CD19)-L-VH(CD19),
wherein:
VH(CD19) and VL(CD19) represent a VH region and a VL region, respectively, which associate with one another to form an antigen binding site specifically binding the CD19 antigen via an epitope of the CD19 antigen;
VH(CD3) and VL(CD3) represent a VH region and a VL region, respectively, which associate with one another to form an antigen binding site specifically binding the CD3 antigen via an epitope of the human CD3 antigen;
"L" and "S" are as defined above.

Within this embodiment, the term "substantially equivalent to" is understood to comprise amino acid sequences homologous to any of SEQ ID NOs: 1-6 by at least 70%, based on a comparison of primary amino acid sequence. Such degrees of homology may be determined by standard sequence alignment programs such as Vector NTI (InforMax™, Maryland, USA). Such programs compare aligned sequences on an amino acid-by-amino acid basis, and can be set to various levels of stringency for the comparison (e.g. identical amino acid, conservative amino acid substitution, etc.). Within the meaning of this embodiment, two amino acids in question are considered as being "homologous" when they are either identical to one another or conservative substitutions of one another. By way of non-limiting example, two different amino acids belonging to the class of lipophilic amino acids would be considered homologous in the sense of this embodiment, even if these two amino acids were not identical, whereas a lipophilic amino acid on the one hand and a charged acidic amino acid on the other hand would not be considered homologous.

In another preferred embodiment of the invention the composition comprises a polypeptide in which the other of the at least two antigen binding sites, i.e. the antigen binding sites which does not specifically bind the human CD3 antigen, specifically binds the human EpCAM ("Epithelial cell adhesion molecule", also called 17-1A antigen, KSA, EGP40, GA733-2, ks1-4 or esa) antigen. EPCAM is a 40 kDa membrane integrated glycoprotein of 314 amino acids with specific expression in certain epithelia and on many human carcinomas. EPCAM has been shown in various studies to be beneficial in diagnosis and therapy of various carcinomas. Furthermore, in many cases, tumor cells were observed to express EpCAM to a much higher degree than their parental epithelium or less aggressive forms of said cancers.

In order to obtain a composition according to the invention starting from a composition comprising polypeptide in both monomeric and multimeric form, it is often necessary to adjust the amount (i.e. weight present in the composition) of polypeptide in monomeric form relative to the amount (i.e. weight present in the composition) of polypeptide in multimeric form. As the weight of the polypeptide in multimeric form in untreated compositions, for example cell harvest lysates obtained following protein expression, will often exceed 5% of the total weight of the combined monomeric and multimeric forms of the polypeptide, it will often be necessary to enrich the content of the polypeptide in monomeric form relative to the content of the polypeptide in multimeric form to obtain the composition of the invention. In general, possibilities include high resolution ion-exchange HPLC, high resolution size exclusion chromatography, gel purification, control of protein expression conditions (e.g. choice of expression host, growth conditions applied to host, expression vector used, type of promoter used, etc.). Advantageous particulars are provided in the examples appended hereto.

In order to accomplish the enrichment mentioned above, another aspect of the invention provides a method of producing a composition in which the amount of a polypeptide in monomeric form has been enriched relative to the amount of said polypeptide in multimeric form. The method comprises the following steps:

a) providing the composition comprising said polypeptide in both multimeric and monomeric form;
b) isolating said polypeptide in both multimeric and monomeric form from said composition, said isolating accomplished by
   (b1) applying said composition to a first chromatographic material comprising a metal ion;
   (b2) removing any components of said composition which have not bound to said first chromatographic material by washing said first chromatographic material with a first buffer; and
   (b3) eluting said polypeptide in both multimeric and monomeric form from said first chromatographic material by applying imidazole to said first chromatographic material in a concentration of at least 60 mM;
   (b4) collecting a first eluate comprising said polypeptide in multimeric form and said polypeptide in monomeric form;
c) performing a precursor step that is preparatory for the separation of said polypeptide in multimeric form from said polypeptide in monomeric form to occur in step (d), said precursor step accomplished by
   (c1) applying said first eluate to a second chromatographic material, which is an ion exchange material;
   (c2) removing any components of the first eluate which have not bound to said second chromatographic material by washing said second chromatographic material with a second buffer;
   (c3) eluting said polypeptide in multimeric and monomeric form from said second chromatographic material by applying sodium chloride to said second chromatographic material in a concentration of at least 200 mM;
   (c4) collecting a second eluate;
d) performing a separation of said polypeptide in multimeric form from said polypeptide in monomeric form, said separation accomplished by
   (d1) applying said second eluate to a third chromatographic material allowing separation on the basis of molecular weight;
   (d2) translocating components of the applied second eluate along said third chromatographic material by applying a running buffer to said third chromatographic material;
   (d3) collecting a third eluate in fractions;
e) analyzing said fractions of said third eluate individually to obtain a measure of the amount of said polypeptide in monomeric form relative to the amount of polypeptide in multimeric form in each fraction; and
combining fractions of said third eluate which (almost) exclusively contain the polypeptide in monomeric form to obtain a composition enriched in the polypeptide in the monomeric form.

Within the meaning of the invention, the term "a composition that is enriched in the monomeric form of the polypeptide" and the like is any composition, the monomer: multimer ratio of which has been adjusted to conform with the present invention. This might be an untreated cell lysate as obtained following recombinant polypeptide production or a composition which already has undergone some degree of enrichment, but which still does not meet the desired criteria vis a vis the ratio of monomeric to multimeric forms of polypeptide present.

It is contemplated that the "first chromatographic material" and "second chromatographic material" are used as part of a batch process or in a chromatography column. Preferably, chromatography columns will be used. One of ordinary skill in the art will be familiar with the selecting, packing and preparing of such chromatography columns prior to chromatography of proteins.

According to a preferred embodiment of the above method, the first chromatographic material comprising a metal ion is a chromatographic material comprising a divalent metal ion, for example the $Ni^{2+}$ or $Zn^{2+}$ ion. An advantageous first chromatographic material is Fractogel® EMD Chelating (Merck), which has been previously charged with $Zn^{2+}$. Using such a first chromatographic material, it is advantageously possible to isolate the polypeptide, whether in monomeric or multimeric form, from the extraneous components typically present in, for example, an untreated cell lysate. Co-expression of a functional marker as part of the polypeptide, for example a His-tag or a Flag-tag may facilitate this isolation.

According to another preferred embodiment, the second chromatographic material allows separation on the basis of anion exchange. An advantageous second chromatographic material in this regard is Q Sepharose HP (Amersham Biosciences).

As is typical in protein chromatography, it is advantageous to equilibrate the chromatographic materials, preferably packed into columns, with a buffer prior to actually performing the protein chromatography. After application of the composition or eluate to be isolated or separated to the chromatographic material, this same buffer is used to wash away any material which has failed to bind to the chromatographic material. The volume of first and second buffers used for washing unbound substances from, respectively, the first and second chromatographic materials advantageously corresponds to 6 to 10 times, preferably of 6 times the volume of the respective chromatographic material used. The volume of the running buffer used for translocating substances along the third chromatographic material advantageously corresponds to 1 to 2 times, preferably 1 time the volume of the chromatographic material used. Phosphate buffer (pH 8) is advantageous as both the first buffer and the second buffer, while either phosphate buffer (pH 7.0-7.5) or citrate/lysine buffer (pH 6.0-7.5) is advantageous as the running buffer.

According to a further embodiment of the inventive method, said method comprises the additional step of analyzing the composition obtained in step (e). In this way, one can obtain a measure of the amount of said polypeptide in monomeric form relative to the amount of polypeptide in multimeric form in the composition. If desired or determined necessary, a further enrichment may ensue by repeating steps (d) through (e). In such a repetition, the composition resulting from the previous round of enrichment is applied to the third chromatographic material in place of the second eluate. Thus, the process of enriching the monomeric form of the polypeptide such that this form is present in no more than the prescribed or desired proportion within the composition can be an iterative procedure which can be repeated as often as necessary or desired until a given degree of enrichment in the amount of the polypeptide in monomeric form has been reached. Typically, however, one round of enrichment should be sufficient to generate a composition conforming to the criteria set for the composition as defined herein.

It is advantageous to perform such optional analysis using a chromatographic method which separates substances on the basis of their molecular weight. Preferably, such a chromatographic method is high performance size exclusion chromatography performed on an HPLC apparatus. One of ordinary skill in the art will understand how to adjust such HPLC parameters as flow rate, pressure and nature of the mobile phase buffer used. Subsequent analysis by size exclusion HPLC has the advantage that relative amounts of monomeric and multimeric forms of polypeptide can be determined with a high degree of accuracy and sensitivity.

In the inventive method, said imidazole in step (b3) may be applied as a single concentration, or may be applied as a concentration gradient ranging from 60 to e.g. 300 mM. Likewise, said sodium chloride in step (c3) may be applied to the second chromatorgraphy material as a single concentration, or may be applied as a concentration gradient ranging from 200 to e.g. 500 mM. Such concentration gradients may be a stepwise gradient, i.e. a gradient in which the concentration of, for example, 60 mM imidazole/200 mM sodium chloride is maintained for a period of time before changing to a concentration of, for example, 70 mM/220 mM sodium chloride, which is maintained for a period of time before changing to the next concentration, and so on. The concentration gradient may also be a non-stepwise gradient, i.e. a gradient in which the concentration of imidazole/sodium chloride is increased at a constant linear rate over time. In the event that a single concentration of imidazole is used, advantageous concentrations are 70 mM, 80 mM, 90 mM, 100 mM, 110 mM or 120 mM. In the event that a single concentration of sodium chloride is used, advantageous concentrations are 370 mM, 380 mM, 390 mM, 400 mM, 410 mM or 420 mM.

In an especially advantageous embodiment of the invention, the imidazole is applied in a single concentration of 80 mM to the first chromatographic material. In another advantageous embodiment of the invention, the sodium chloride is applied in a single concentration of 400 mM to the second chromatographic material. A combination of these advantageous embodiments is particularly preferred. Application of imidazole and sodium chloride in the above respective concentrations has the advantageous effect that the distribution of the monomeric form of the polypeptide and the closest eluting species of the multimeric form of the polypeptide, namely the dimeric form of the polypeptide, are resolved as two distinct, i.e. non-overlapping peaks of polypeptide in the subsequent second separation step (d). Separation of two polypeptide species, here the monomeric and dimeric forms of the polypeptide, with such baseline resolution allows the monomeric form of the polypeptide to be obtained in higher yield free from impurities of the corresponding dimeric form of the polypeptide. This in turn increases the likelihood of obtaining fractions from the second separation containing exclusively or predominantly the polypeptide in monomeric form. As such, the advantageous resolution achieved by the above two concentrations of imidazole and sodium chloride used in concert increases the efficiency with which a composition enriched with respect to the monomeric form of the polypeptide may be obtained.

A further aspect of the invention is a composition (obtainable by the above method of obtaining a composition) which is enriched in the monomeric relative to the multimeric form of the polypeptide.

Another aspect of the invention provides a method for the prevention, treatment or amelioration of a proliferative disease, of a minimal residual cancer, of a tumorous disease, of an inflammatory disease, of an immunological disorder, of an autoimmune disease, of an infectious disease, of a viral disease, of an allergic reaction, of a parasitic reaction, of a graft-versus-host disease, of a host-versus-graft disease or of a B cell malignancy. According to this aspect, the composition as disclosed hereinabove is administered to a subject in need of such a prevention, treatment or amelioration.

A further aspect of the invention provides a use of the composition as disclosed herein above for the production of a medicament for the prevention, treatment or amelioration of a proliferative disease, of a minimal residual cancer, of a tumorous disease, of an inflammatory disease, of an immunological disorder, of an autoimmune disease, of an infectious disease, of a viral disease, of an allergic reaction, of a parasitic reaction, of a graft-versus-host disease, of a host-versus-graft disease or of a B cell malignancy.

According to a preferred embodiment, the prevention, treatment or amelioration occurs in a human. The tumorous disease is preferably selected from the group consisting of a lymphoma, a B cell lymphoma and a Hodgkin lymphoma. In a further embodiment, the B cell lymphoma is non-Hodgkin lymphoma. In a further embodiment, the autoimmune disease is selected from rheumatoid arthritis, multiple sclerosis, type I diabetes mellitus, inflammatory bowel disease, systemic lupus erythematosus, psoriasis, scleroderma and autoimmune thyroid diseases.

Throughout the instant application, it is to be understood that use of a term in the singular may imply, where appropriate, use of the respective term in the plural. Similarly, use of a term in the plural may imply, where appropriate, use of the respective term in the singular.

The invention will now be described further by the appended figures and examples.

EXAMPLES AND DETAILED DESCRIPTION OF THE FIGURES

Example 1: Polypeptide Production

Figure 1:
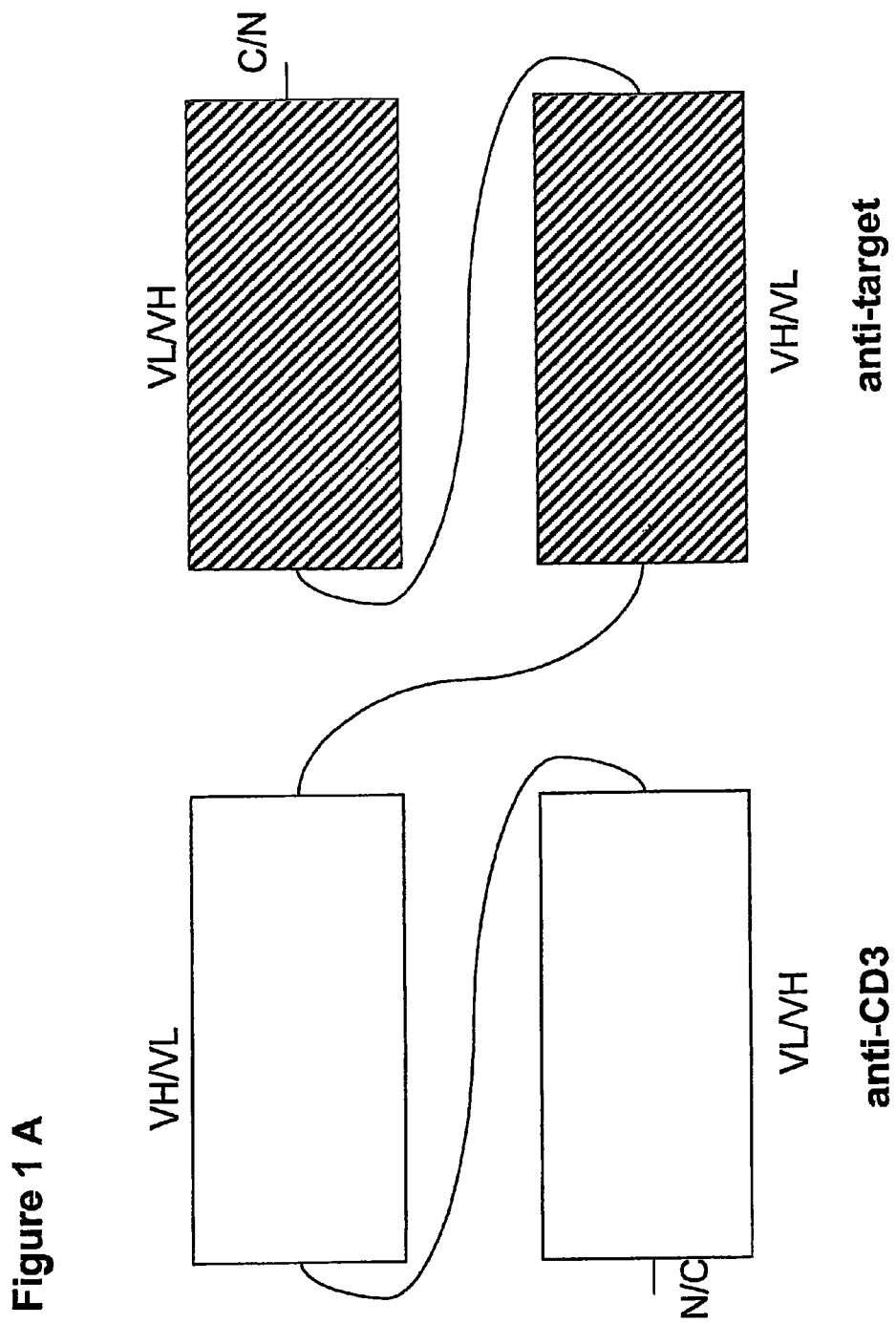
FIG. 1A: Model of a polypeptide comprising two antigen binding sites, wherein one antigen binding site specifically binds the human CD3 antigen, and wherein the polypeptide exists in monomeric form
FIG. 1B: Model of a polypeptide comprising two antigen binding sites, wherein one antigen binding site specifically binds the human CD3 antigen, and wherein the polypeptide exists in multimeric (here, dimeric) form due to association of two-individual target antigen binding sites.
FIG. 1C: Model of a polypeptide comprising two antigen binding sites, wherein one antigen binding site specifically binds the human CD3 antigen, and wherein the polypeptide exists in multimeric (here, dimeric) form due to association of two individual effector antigen binding sites specific for the human CD3 antigen.
Figure 1:
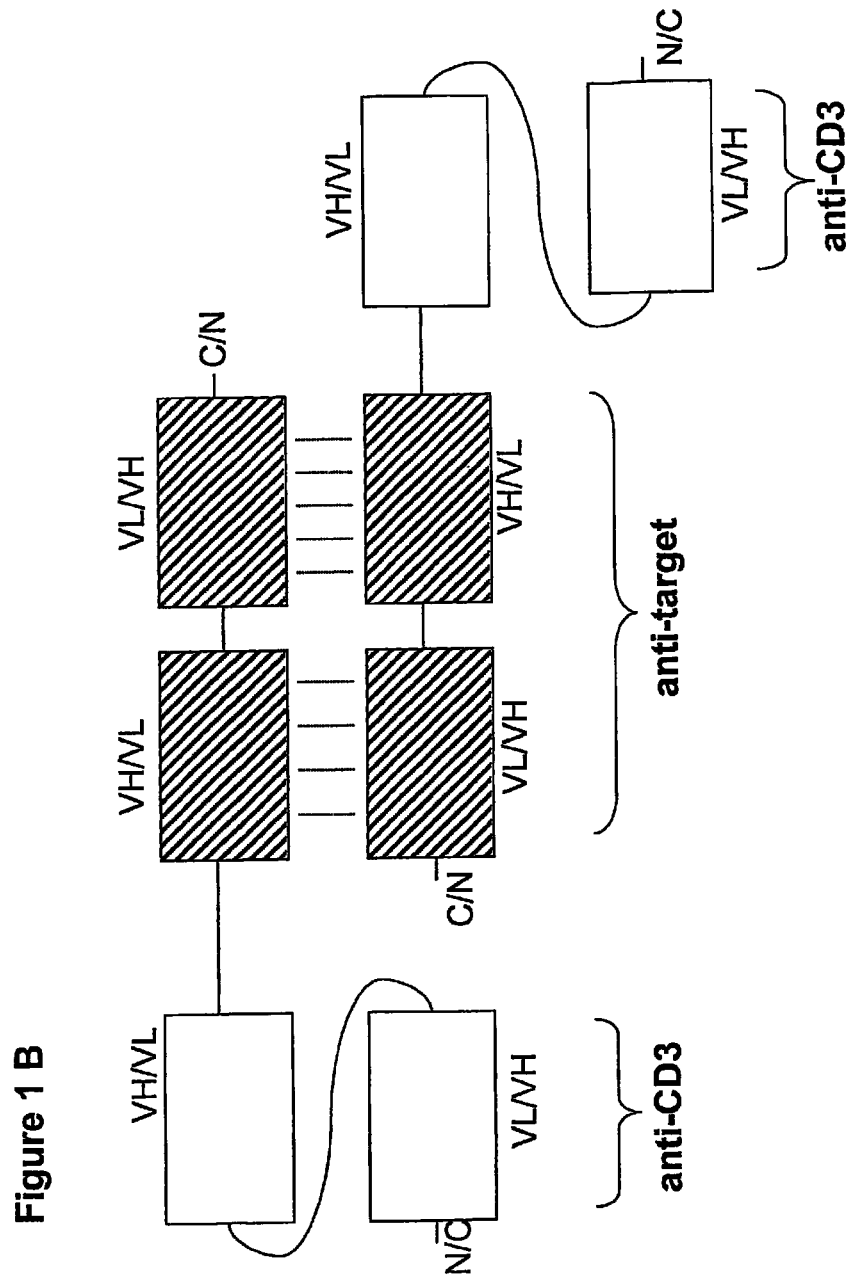

Starting from suitable eukaryotic expression vectors, expression of a polypeptide comprising two antigen binding sites is performed in CHO cells in a stirred tank bioreactor using a serum- and protein-free medium. Fermentation is conducted in fed-batch mode at 37° C. with glucose feeding. Upon completion of the fermentation process, the supernatant containing secreted polypeptide is harvested by dead end filtration and concentrated 10-fold by cross flow filtration.

The following describes how the ratio of the amount of polypeptide in monomeric form to the amount of polypeptide in multimeric form may be adjusted. As a model for such adjustment, the anti-CD19×anti-CD3 polypeptide according to SEQ ID NO. 1 (hereinafter "Construct 1") is used, and the multimeric form of Construct 1 is the dimeric form of Construct 1.

Capture of Construct 1 from the cell harvest is performed using an immobilized metal affinity chromatography column (Fractogel EMD Chelating, Merck) charged with zinc ($Zn^{2+}$-IMAC). The column is equilibrated with 2 column volumes (CV) of phosphate buffer, the cell harvest is applied at 120-180 cm/h and unbound material is washed away with 6 CV of buffer. Applying a step gradient with 60-300 mM Imidazole in phosphate buffer over 5 CV elutes the product. Alternatively, an individual concentration of 70 mM, 80 mM, 90 mM, 100 mM, 110 mM or 120 mM imidazole may be used for this purpose. Intermediate purification of Construct 1 is performed employing anion exchange chromatography (AIEX, Q Sepharose HP, Amersham Biosciences). The column is equilibrated with 2 CV of phosphate buffer pH 8.0 and the eluate from the IMAC column is directly applied to the column. Unbound protein is removed by washing with 6 CV buffer. The product is subsequently eluted with a step gradient of 6 CV of 200-500 mM sodium chloride in buffer. Alternatively, an individual concentration of 370 mM, 380 mM, 390 mM, 400 mM, 410 mM or 420 mM sodium chloride may be used for this purpose. Final adjustment is performed by size exclusion chromatography (SEC) including a separation of monomeric and dimeric forms of Construct 1. A Superdex 200 prep grade column (Amersham Biosciences, bed height >600 mm) is equilibrated with at least 4 CV of either phosphate buffer pH 7.0-7.5 or citrate/lysine buffer pH 6.0-7.5. The sample (corresponding to a volume of 1-5% of the CV) is applied to the column and an isocratic elution using the equilibration buffer is performed. The dimer elutes at approximately 0.5-0.6 CV while the monomer elutes at approximately 0.6 to 0.7 CV (exact elution conditions may vary depending on column length, sample volume, and quality of the column packing). Eluted polypeptide is fractionated and desired fractions are combined. Later fractions contain a higher amount of Construct 1 in monomeric form than do earlier fractions. The ratio of the amount of monomeric Construct 1 to the amount of dimeric Construct 1 may therefore be influenced by the choice of the fraction used.

Specific combinations of elution parameters have proven to be very advantageous. Specifically, elution of the polypeptide, for example Construct 1, from the $Zn^{2+}$-IMAC column with a single concentration of 80 mM imidazole followed in the next step by elution of this polypeptide from the anion-exchange column with a single concentration of 400 mM sodium chloride yields a mixture of polypeptide which, when resolved by size exclusion chromatography as described above, results in the monomeric form of the polypeptide being baseline-resolved from the next largest multimeric form of the polypeptide, namely the dimeric form of the polypeptide. This lack of overlapping shoulders of peaks corresponding to monomeric and dimeric forms of the polypeptide facilitates the obtaining of fractions containing exclusively or predominantly the monomeric form of the polypeptide; these fractions may later be combined to obtain a mixture in which the content of the monomeric form of the polypeptide has been enriched relative to the content of multimeric or, here, dimeric form of the polypeptide.

As an alternative, cation- or anion-exchange chromatography or chromatography on hydroxyapatite may be used to separate monomeric polypeptide from multimeric, especially from dimeric polypeptide. In both cation and anion exchange chromatography the dimeric form of the polypeptide elutes later during gradient elution. For separation of monomer and dimer using ion exchange, the eluate from the anion exchange column should be diluted. For cation exchange, the pH should be adjusted to allow binding of polypeptide. When using hydroxyapatite chromatography, a low conductivity phosphate buffer should be used.

Analysis of the ratio of relative amounts of monomeric to multimeric polypeptide in a given mixture may be performed by SEC-HPLC using e.g. an Agilent 1100 series HPLC system (or similar). The column used is a Tosoh Biosep TSKgel G3000SWXL column with guard column at a flow rate of 0.6-0.75 mL/minute at a maximum Pressure of 75 bar ($7.5 \times 10^6$ Pa). As mobile phase a buffer of 100 mM KH2PO4/KOH, 200 mM Na2SO4 pH 6.6 is used. 100 μL of sample are applied. The total run time is 27 minutes. Wavelength of detection is set to 210 nm.

Example 2: Additional Biological Activities Attributable to the Polypeptide in Multimeric Form but not to the Polypeptide in Monomeric Form A polypeptide comprising two antigen binding sites, one of which specifically binds the human CD3 antigen, is able to bind to (and activate the cytotoxic activity of) cytotoxic T cells via the CD3 antigen located on the surface of such cytotoxic T cells. At the same time, such a polypeptide can specifically bind with its target binding site a surface target on, for example, tumor cells, which would normally not be recognized by cytotoxic T cells. In this manner, the cytotoxic activity of T cells can be directed to, for example, tumor cells as part of a therapeutic regimen to eliminate such cells. Ideally, cytotoxic T cells are only activated upon interaction with a target cell mediated by the polypeptide molecule described above. While the activation mechanism described above seems to be the only biological activity observed for the polypeptide in monomeric form (as defined hereinabove), the polypeptide in multimeric form (as defined hereinabove) has been observed to exhibit additional biological activities.

Polypeptides comprising two antigen binding sites, of which one antigen binding site specifically binds the human CD3 antigen, have a tendency to dimerize.

The following examples therefore discuss the nature of these additional biological activities observed for the polypeptide in multimeric form, using the polypeptide in dimeric form as a concrete example.

FIG. 1A depicts a polypeptide in monomeric form as comprised in the composition of the present invention. The antigen binding sites of the polypeptide are each derived from different antibodies, and each comprises a VH and VL region. The designations "VH/VL" and "VL/VH" denote a mutually exclusive option of either VH or VL at the region so designated. Hence a region designated "VH/VL" would be expected to associate with a region designated "VL/VH" since the two possible associations would result in either, from amino- to carboxy-terminus, VH associating with VL or VL associating with VH. The polypeptide in monomeric form depicted in FIG. 1a would be expected to specifically bind the human CD3 antigen with the left-hand antigen binding site, and another target antigen with the right-hand antigen binding site. The polypeptide may therefore act as a bridge specifically linking a cytotoxic T cell with a target cell of interest while directing the cytotoxic activity of the cytotoxic T cell against the target cell as described hereinabove.

FIG. 1B depicts one possible model for the polypeptide comprised in the present invention, wherein this polypeptide is in multimeric form. Here, the specific polypeptide shown is in dimeric form, meaning that two single polypeptide chains have non-covalently associated to form a homodimeric species. FIG. 1B depicts the scenario in which the two single polypeptide chains have non-covalently associated in an antiparallel fashion through their antigen binding sites which specifically bind target antigen. It should be noted that in this model of dimer formation, the antigen binding sites which specifically bind the human CD3 antigen (each designated "anti-CD3") are free to bind two separate human CD3 antigens (one human CD3 antigen is specifically bound by each anti-CD3 binding site). In contrast, the antigen binding site which specifically binds to target antigen (designated "anti-target") present on one single polypeptide chain is non-covalently associated with the "anti-target" binding site present on the other single polypeptide chain, so that neither of these two target antigen binding sites may specifically bind target antigen. As such, the polypeptide in dimeric form depicted in FIG. 1B would be capable of simultaneously and specifically binding two individual human CD3 antigens, but would be less capable of binding a target antigen.

Figure 1C:
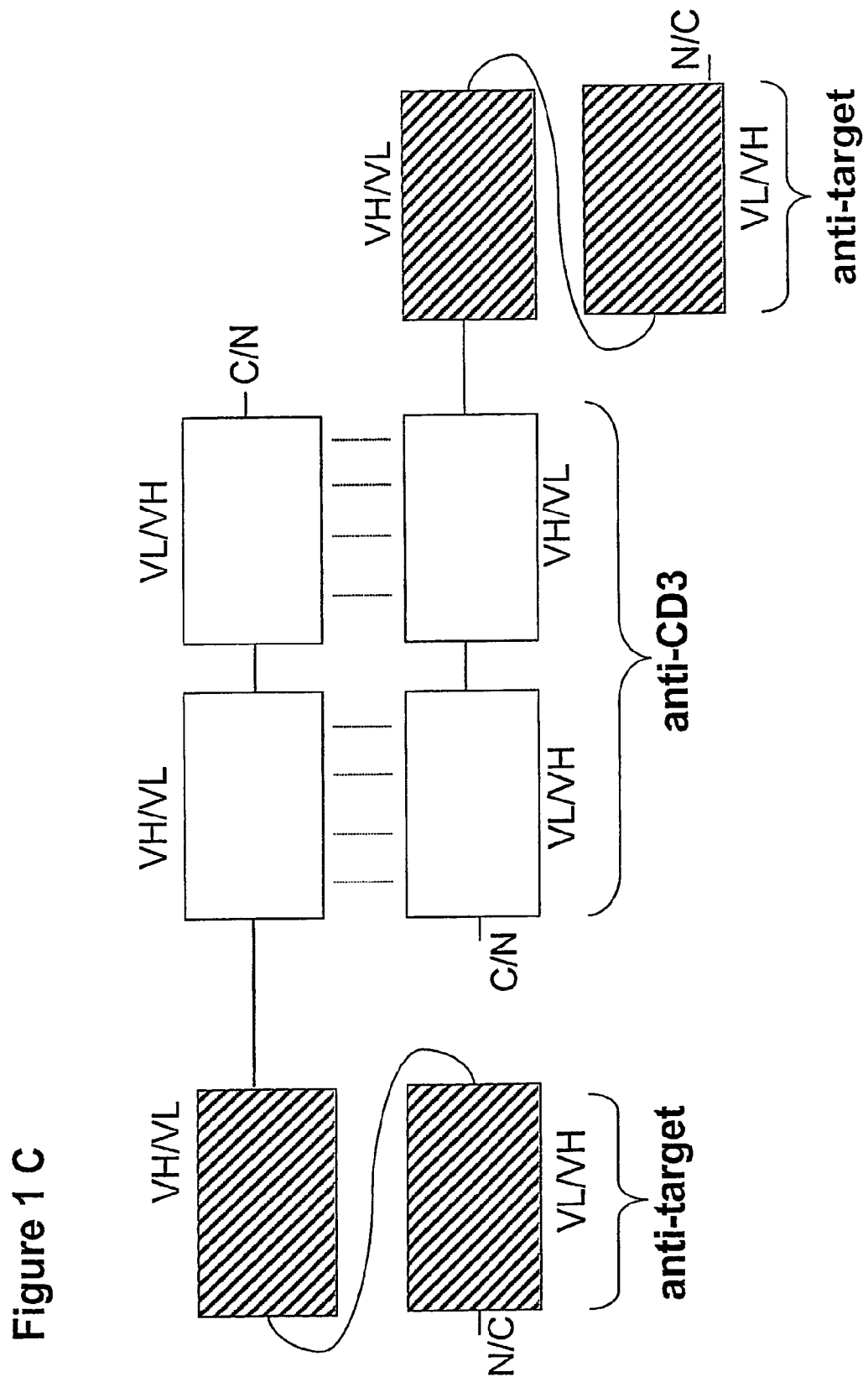

FIG. 1C depicts another possible model for the polypeptide comprised in the present invention, wherein this polypeptide is in multimeric form. Here, the specific polypeptide shown is in dimeric form, meaning that two single polypeptide chains have non-covalently associated to form a homodimeric species. FIG. 1B depicts the scenario in which the two single polypeptide chains have non-covalently associated in an antiparallel fashion through their effector binding sites which specifically bind the human CD3 antigen. It should be noted that in this model of dimer formation, the antigen binding sites which specifically bind the target antigen (each designated "anti-target") are free to bind two separate target antigens (one target antigen is specifically bound by each anti-target binding site). In contrast, the antigen binding site which specifically binds to the human CD3 antigen (designated "anti-CD3") present on one single polypeptide chain is non-covalently associated with the "anti-CD3" binding site present on the other single polypeptide chain, so that neither of these two antigen binding sites may specifically bind the human CD3 antigen. As such, the polypeptide in dimeric form depicted in FIG. 1C would be capable of simultaneously and specifically binding two individual target antigens, but would be less capable of binding a human CD3 antigen.

Example 2a: Activation of T Cells by Polypeptide in Multimeric (Here, Dimeric) Form in the Absence of Target Cells Peripheral blood mononuclear cells (PBMCs) were prepared from blood of a healthy donor by Ficoll density centrifugation. To investigate whether the polypeptide of the inventive composition in multimeric (here, dimeric) form is capable of activating T cells in the absence of target cells, PBMCs were incubated with a polypeptide comprising two antigen binding sites. One antigen binding site (the effector binding site) of the polypeptide specifically bound the human CD3 antigen, and the other antigen binding site (the target antigen binding site) of the polypeptide specifically bound the human EpCAM antigen. This particular polypeptide was chosen for study because the interaction with target cells could be excluded due to the absence of EpCAM-positive cells in the PBMC population; any effects observed in using the above polypeptide with PBMCs would be attributable solely to the binding site specifically binding the human CD3 antigen.

In order to compare the effect of polypeptide in monomeric form with the effect of polypeptide in dimeric form, the polypeptide had previously been resolved into fractions containing either exclusively monomeric polypeptide (as for example modeled in FIG. 1A) or exclusively dimeric polypeptide (as for example modeled in FIGS. 1B and 1C). Resolution of polypeptide into these fractions was accomplished as described above in Example 1.

Figure 2:
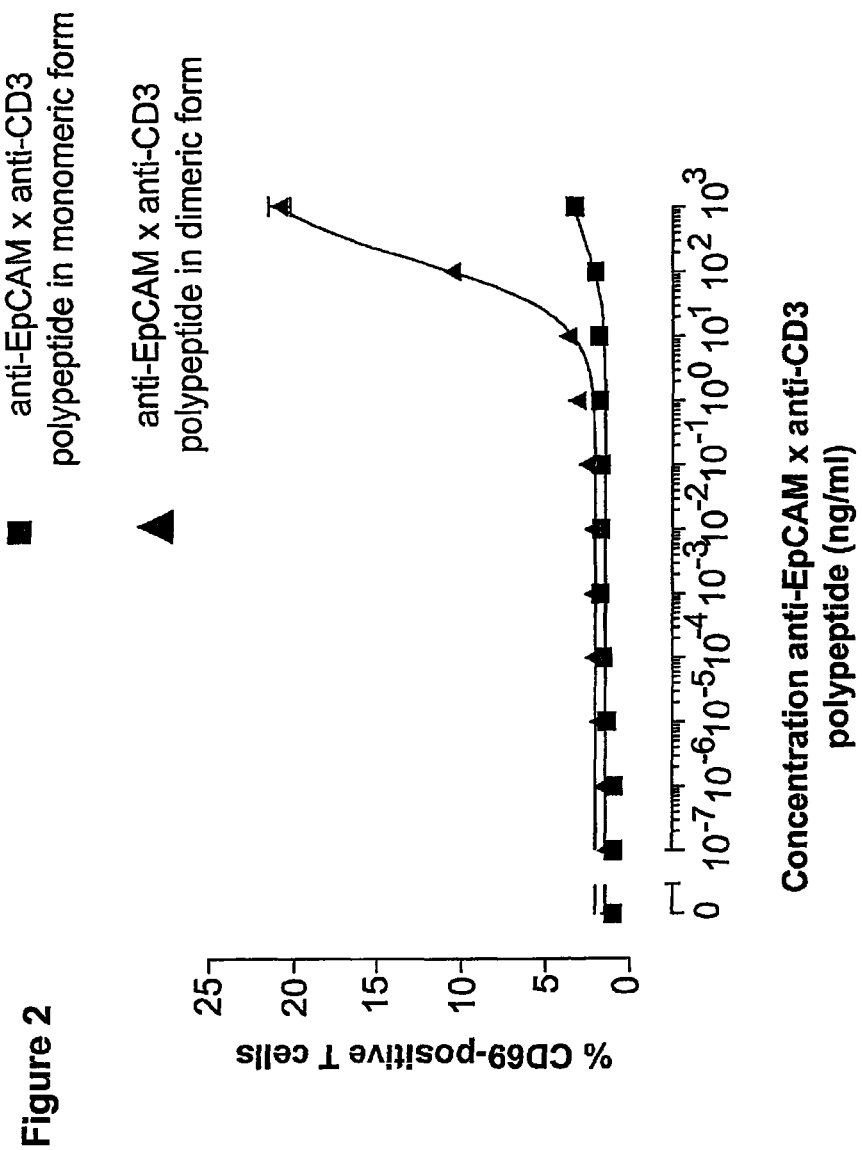
FIG. 2: Up-regulation of the early T cell marker CD69 as a function of concentration of polypeptide in monomeric and multimeric (here, dimeric) form

In round-well microtiter plates, $2 \times 10^5$ PBMCs/well were incubated in a volume of 200 μL with either pure monomer or pure dimer fractions of the polypeptide at the concentrations indicated in FIG. 2. Using flow cytometry, the expression levels of CD69 were analyzed in each sample after a 24-hour incubation period. CD69 is a marker on the surface of T cells, the up-regulation of which can serve as an early indicator of T cell activation. By monitoring the expression levels of CD69 in the various samples, it is possible to obtain an early measure of the degree to which the activation of T cells has taken place. T cells were identified with an anti-CD3-specific antibody. Samples were analyzed in duplicate.

As can be seen in FIG. 2, incubation with the polypeptide in dimeric form resulted in more than 20% of T cells being activated at a polypeptide concentration of 1 µg/mL. The lowest concentration of polypeptide in dimeric form eliciting an expansion of CD69-positive T cells was 10 ng/mL. In contrast, the polypeptide in monomeric form induced CD69 expression of only about 3% of the T cells at the highest tested concentration (1 µg/mL of polypeptide in monomeric form). The minimal degree of activation observed in response to the polypeptide in monomeric form at a concentration of 1 µg/mL might be a result of residual polypeptide in dimeric form still present in the preparation of polypeptide in monomeric form. These data demonstrate that the polypeptide in dimeric form is able to activate T cells in the absence of target cells while the monomer is not. This capability represents an activity other than the killing of target cells which is attributable to the polypeptide in dimeric form but not to the polypeptide in monomeric form.

Example 2b: Mutual T Cell Lysis by Polypeptide in Multimeric (Here, Dimeric) Form To analyze whether the polypeptide in multimeric (here, dimeric) form is capable of killing T cells two sets of experiments were performed in which effector cells were co-incubated with the T cell line HPBALL (DSMZ No ACC 483; DMSZ=Deutsche Sammiung von Mikroorganismen und Zelikulturen GmbH) in the presence of polypeptide. In the first set of experiment, PBMCs were used as the effector cells, whereas the effector cells used in the second set of experiments were MC15 cells (Biesinger B., Müller-Fleckenstein I., Stimmer B., Lang G., Wittmann S., Plater E. Desrosiers R. C. and Fleckenstein B.; 2002, Proc. Natl. Acad. Sci. USA, 89, 3116-3119).

The polypeptide used for this experiment comprised two antigen binding sites. One antigen binding site (the effector binding site) specifically bound the human CD3 antigen, and the other antigen binding site specifically bound the human CD19 antigen, a pan-B cell marker described hereinabove. HPBALL cells have been described to be CD3-positive. Blood cells were washed out from Leukocyte filters. PBMCs were prepared by Ficoll density centrifugation. MC15 cells were cultured as described in the literature reference above in this paragraph. To distinguish the effector cells from target cells, the HPBALL cells were stained with the fluorescent dye Calcein AM according to the manufacturer's protocol.

In order to compare the effect of polypeptide in monomeric form with the effect of polypeptide in dimeric form, the polypeptide had previously been resolved into fractions containing either exclusively monomeric polypeptide (as for example modelled in FIG. 1A) or, exclusively dimeric polypeptide (as for example modelled in FIGS. 1B and 1C). Resolution of polypeptide into these fractions was accomplished as described above in Example 1.

Figure 3A:
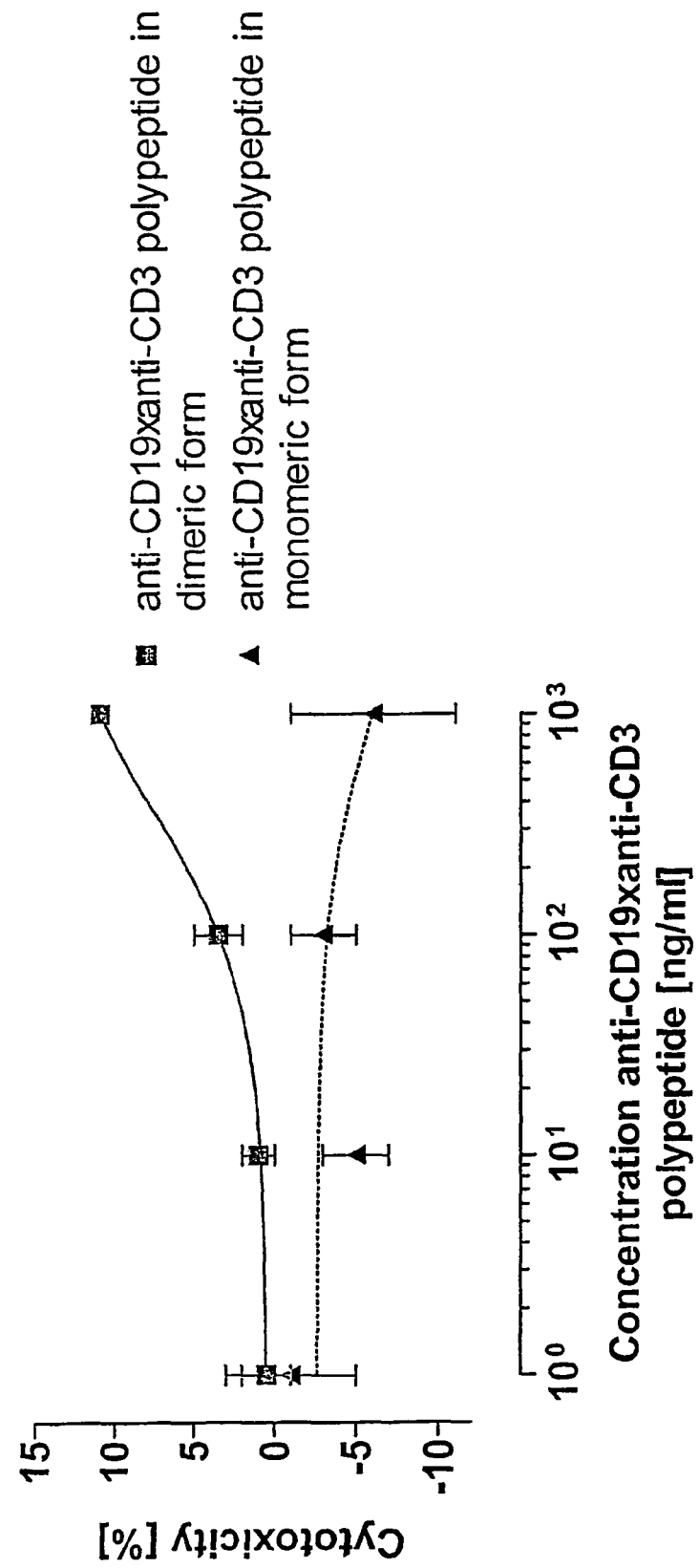
FIG. 3A: Mutual T cell lysis as a function of concentration of polypeptide in monomeric and multimeric (here, dimeric) form using PBMCs as effector cells
Figure 3B:
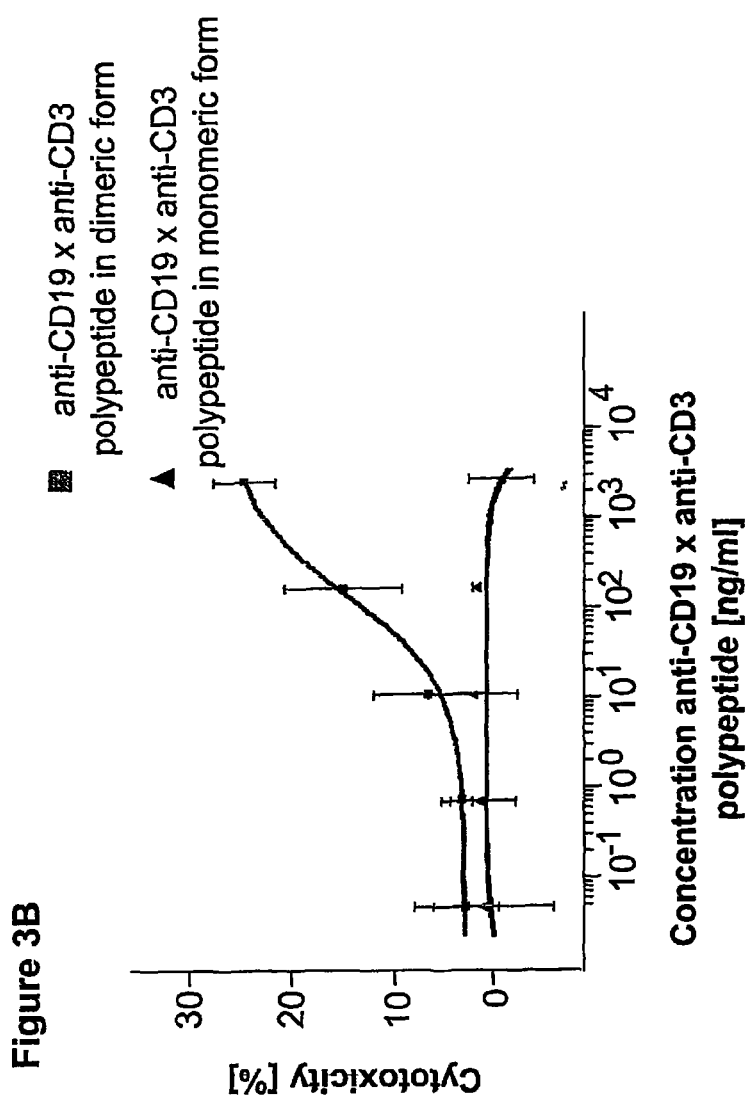
FIG. 3B: Mutual T cell lysis as a function of concentration of polypeptide in monomeric and multimeric (here, dimeric) form using MC15 cells as effector cells

In round-bottom microtiter plates, $5 \times 10^5$ effector cells were incubated with $5 \times 10^4$ HPBALL cells for 4 hours in the presence of either highly pure monomer or highly pure dimer fractions of the above polypeptide at the concentrations indicated in FIG. 3A (for PBMC effector cells) and FIG. 3B (for MC15 effector cells). Appropriate controls containing HPBALL cells and effector cells were incubated in the absence of polypeptide. After the incubation period the supernatants were harvested. The amount of fluorescent dye released by dead cells was measured using a Spectrafluorometer. As can be seen in each of FIG. 3A and FIG. 3B, the polypeptide in dimeric form induced HPBALL cell lysis at concentrations higher than 10 ng/mL. In contrast, no target cell lysis by the polypeptide in monomeric form was observed under identical conditions. This finding demonstrates that lysis of CD3-positive cells has occurred and is attributable to the polypeptide in dimeric form but not to the polypeptide in monomeric form.

Example 3: General Propensity of Polypeptides to Form Dimers

It was desired to show that the propensity to form a multimeric species is common to the general class of bispecific single chain antibodies in which one binding specificity is for the human CD3 antigen. To this end, a number of such bispecific antibodies were produced in Chinese hamster ovary (CHO) cells according to generally known procedures (Sambrook et al., 1989). Each bispecific single chain antibody produced contained two antigen binding sites, each antigen binding site containing one VH and one VL antibody region. One of the two antigen binding sites in each molecule was specific for the human CD3 antigen. The other antigen binding site ("target antigen binding site") was specific for a desired target antigen other than the human CD3 antigen. Proportions of polypeptide in monomeric and multimeric (here, dimeric) form were determined by a combination of SDS-PAGE performed under reducing conditions, Western Blot performed using Penta-His (Qiagen) and Goat-anti-mouse-AP (Sigma) antibodies and gel filtration performed on a Sephadex S200 column. The relative proportions of bispecific single chain polypeptide present in dimeric form are shown below in Table 1 for polypeptides comprising target antigen specificities against the human CD19 antigen, the human EpCAM antigen, the human Wue1 antigen (a highly specific multiple myeloma antigen) and the human sTn antigen (a carbohydrate displayed on the epithelium of malignant cells in breast, prostate and colon cancers).

TABLE 1

| Target antigen specificity | Approximate % of single polypeptide chains present as a monomer | Approximate % of single polypeptide chains present as a dimer |
|---|---|---|
| CD19 ("Construct 1" from above) | ~65-70% | ~30-35% |
| EpCAM | ~75% | ~25% |
| Wue1 | ~85-90% | ~10-15% |
| sTn | ~75-80% | ~20-25% |

As can clearly be seen in Table 1, each bispecific single chain antibody with anti-human CD3 antigen binding specificity spontaneously forms significant amounts of multimeric (i.e. here, dimeric) species when left uncontrolled. The propensity to spontaneously form homodimers therefore appears to be a generic characteristic of the class to which the bispecific single chain antibodies examined here belong.

The invention claimed is:

1. A pharmaceutical composition that simultaneously binds CD3 and CD19, the composition comprising a single polypeptide chain comprising the amino acid sequence set forth in any one of SEQ ID NOS: 1-6 and a citrate/lysine buffer pH 6.0-7.5, wherein the polypeptide is present in the composition
in both monomeric form and multimeric form, said monomeric form being a single polypeptide chain and said multimeric form comprising at least two single polypeptide chains non-covalently associated with one another, wherein said multimeric form of said polypeptide constitutes no more than 3% of the total weight of the combined monomeric and multimeric forms of said polypeptide, wherein said pharmaceutical composition is obtained by
a) providing a composition comprising said polypeptide in both multimeric and monomeric form obtained from expression of said polypeptide in CHO cells;
b) isolating said polypeptide in both multimeric and monomeric form from said composition, said isolating is accomplished by
   i) applying said composition to a first chromatographic material comprising a metal ion, which is a $Zn^{2+}$ or $Ni^{2+}$ ion;
   ii) removing any components of said composition which have not bound to said first chromatographic material by washing said first chromatographic material with a first buffer;
   iii) eluting said polypeptide in both multimeric and monomeric forms from said first chromatographic material by applying imidazole to said first chromatographic material in a concentration of at least 60 mM; and
   iv) collecting a first eluate comprising said polypeptide in multimeric form and said polypeptide in monomeric form;
c) performing a precursor step that is preparatory for the separation of said polypeptide in multimeric form from said polypeptide in monomeric form to occur in step (d), said precursor step accomplished by
   i) applying said first eluate to a second chromatographic material, which is an ion exchange material;
   ii) removing any components of the first eluate which have not bound to said second chromatographic material by washing said second chromatographic material with a second buffer;
   iii) eluting said polypeptide in multimeric and monomeric form from said second chromatographic material by applying sodium chloride to said second chromatographic material in a concentration ranging from 200 mM to 500 mM; and
   iv) collecting a second eluate;
d) performing a separation of said polypeptide in multimeric form from said polypeptide in monomeric form, said separation accomplished by
   i) applying said second eluate to a third chromatographic material allowing separation on the basis of molecular weight;
   ii) translocating components of the applied second eluate along said third chromatographic material by applying a citrate/lysine buffer pH 6.0-7.5 to said third chromatographic material; and
   iii) collecting a third eluate in fractions;
e) analyzing said fractions of said third eluate individually to obtain a measure of the amount of said polypeptide in monomeric form relative to the amount of polypeptide in multimeric form in each fraction; and
f) combining fractions of said third eluate which contain the polypeptide in monomeric form to obtain a composition such that the multimeric form of said polypeptide constitutes no more than 3% of the total weight of the combined monomeric and multimeric forms of said polypeptide.

2. The composition of claim 1, wherein steps (b)(ii) and/or (c)(ii) is/are performed by means of chromatography on a column or by means of a batch process.

3. The composition of claim 1, wherein said first chromatographic material comprises the $Zn^{2+}$ or the $Ni^{2+}$ ion.

4. The composition of claim 1, wherein said second chromatographic material allows separation on the basis of anion exchange.

5. The composition of claim 1, wherein said washing of steps (b)(ii) and (c)(ii) are performed using a volume of first and/or second buffer which is 6 to 10 times greater than the volume of the first and/or second chromatographic material, respectively.

6. The composition of claim 1, wherein said translocating of step (d)(ii) is accomplished by applying a volume of said running buffer equivalent to 3 to 7 times the volume of the third chromatographic material.

7. The composition of claim 1, wherein said first and second buffer are each phosphate buffer pH 8.

8. The composition of claim 1, wherein said running buffer in step (d)(ii) comprises phosphate buffer pH 7.0-7.5 or citrate/lysine buffer pH 6.0-7.5.

9. The composition of claim 1, wherein said analyzing is performed using a chromatographic method which separates substances on the basis of their molecular weight.

10. The composition of claim 9, wherein said chromatographic method is size exclusion chromatography.

11. The composition of claim 1, wherein:
said imidazole is applied either as a concentration gradient or as a single concentration and/or
said sodium chloride is applied either as a concentration gradient or as a single concentration.

12. The composition of claim 11, wherein:
said imidazole is applied in a single concentration selected from the group consisting of: 70 mIVI, 80 mM, 90 mIVI, 100 mIVI, 110 mIVI and 120 mM; and
said sodium chloride is applied in a single concentration selected from the group consisting of: 370 mM, 380 mM, 390 mM, 400 mIVI, 410 mM and 420 mM.

13. The composition of claim 12, wherein said imidazole is applied in a concentration of 80 mM and/or said sodium chloride is applied in a concentration of 400 mM.

14. The pharmaceutical composition of claim 1, wherein said multimeric form of said polypeptide constitutes no more than 2% of the total weight of the combined monomeric and multimeric forms of said polypeptide.

15. The pharmaceutical composition of claim 1, wherein said multimeric form of said polypeptide constitutes no more than 1% of the total weight of the combined monomeric and multimeric forms of said polypeptide.

* * * * *